US007368469B2

(12) United States Patent
Schölkens et al.

(10) Patent No.: US 7,368,469 B2
(45) Date of Patent: *May 6, 2008

(54) USE OF INHIBITORS OF THE RENIN-ANGIOTENSIN SYSTEM IN THE PREVENTION OF CARDIOVASCULAR EVENTS

(75) Inventors: Bernward Schölkens, Kelkheim (DE); Norbert Bender, Hofheim (DE); Badrudin Rangoonwala, Hofheim (DE); Gilles Dagenais, St.-Nicholas (CA); Hertzel Gerstein, Hamilton (CA); Salim Yusuf, Carlisle (CA)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/490,061

(22) Filed: Jul. 21, 2006

(65) Prior Publication Data
US 2007/0021491 A1    Jan. 25, 2007

Related U.S. Application Data

(63) Continuation of application No. 10/694,001, filed on Oct. 28, 2003, now abandoned, which is a continuation of application No. 09/651,275, filed on Aug. 30, 2000, now abandoned.

(60) Provisional application No. 60/151,436, filed on Aug. 30, 1999.

(51) Int. Cl.
*A61K 31/40* (2006.01)
*A61K 31/60* (2006.01)
*A61K 31/35* (2006.01)

(52) U.S. Cl. .................. 514/412; 514/161; 514/423; 514/451; 514/460

(58) Field of Classification Search ............ None
See application file for complete search history.

(56) References Cited

U.S. PATENT DOCUMENTS

| | | |
|---|---|---|
| 3,983,140 A | 9/1976 | Endo et al. |
| 4,231,938 A | 11/1980 | Monaghan et al. |
| 4,346,227 A | 8/1982 | Terahara et al. |
| 4,444,784 A | 4/1984 | Hoffman et al. |
| 4,448,784 A | 5/1984 | Glamkowski et al. |
| 4,450,171 A | 5/1984 | Hoffman et al. |
| 4,587,258 A | 5/1986 | Gold et al. |
| 4,681,893 A | 7/1987 | Roth |
| 4,722,810 A | 2/1988 | Delaney et al. |
| 4,739,073 A | 4/1988 | Kathawala |
| 4,743,450 A | 5/1988 | Harris et al. |
| 4,749,688 A | 6/1988 | Haslanger et al. |
| 4,804,770 A | 2/1989 | Karanewsky |
| 4,857,520 A | 8/1989 | Urbach et al. |
| 4,975,453 A | 12/1990 | Becker et al. |
| 4,983,598 A | 1/1991 | Cavero et al. |
| 5,061,694 A | 10/1991 | Aberg et al. |
| 5,098,910 A | 3/1992 | Becker et al. |
| 5,130,333 A | 7/1992 | Pan et al. |
| 5,140,012 A | 8/1992 | McGovern et al. |
| 5,157,025 A | 10/1992 | Aberg et al. |
| 5,166,143 A | 11/1992 | Ondetti et al. |
| 5,190,970 A | 3/1993 | Pan et al. |
| 5,196,444 A | 3/1993 | Naka et al. |
| 5,202,322 A | 4/1993 | Allen et al. |
| 5,212,165 A | 5/1993 | Aberg et al. |
| 5,217,958 A | 6/1993 | Patel |
| 5,219,856 A | 6/1993 | Olson |
| 5,223,516 A | 6/1993 | Delaney et al. |
| 5,225,401 A | 7/1993 | Seymour |
| 5,231,080 A | 7/1993 | Schölkens |
| 5,231,083 A | 7/1993 | Linz et al. |
| 5,266,583 A | 11/1993 | Ohtawa |
| 5,273,995 A | 12/1993 | Roth |

(Continued)

FOREIGN PATENT DOCUMENTS

CA    2 026 686    5/1991

(Continued)

OTHER PUBLICATIONS

HOPE Study Investigators, "The HOPE (Heart Outcomes Prevention Evaluation) Study: The design of a large simple randomized trial of an angiotensin-converting enzyme inhibitor (ramipril) and vitamin E in patients at high risk of cardiovascular events," Can. J. Cardiol., vol. 12, No. 2, pp. 127-137 (1996).

(Continued)

*Primary Examiner*—Raymond J. Henley, III
(74) *Attorney, Agent, or Firm*—Finnegan, Henderson, Farabow, Garrett & Dunner, L.L.P.

(57) ABSTRACT

Use of an inhibitor of the renin-angiotensin system or a pharmaceutically acceptable derivative thereof, optionally together with another antihypertensive, a cholesterol lowering agent, a diuretic or aspirin, in the manufacture of a medicament for the prevention of cardiovascular events; a method of preventing cardiovascular events comprising administering to a patient in need of such prevention an effective amount of an inhibitor of the renin angiotensin system or a pharmaceutically acceptable derivative thereof, optionally together with another antihypertensive, a cholesterol lowering agent, a diuretic or aspirin; and a combination product containing an an inhibitor of the renin-angiotensin system or a pharmaceutically acceptable derivative thereof and a cholesterol lowering agent.

94 Claims, No Drawings

U.S. PATENT DOCUMENTS

| | | |
|---|---|---|
| H1286 H | 2/1994 | Eisman et al. |
| 5,298,497 A | 3/1994 | Tschollar et al. |
| 5,308,846 A | 5/1994 | Allen et al. |
| 5,362,727 A | 11/1994 | Robl |
| 5,366,973 A | 11/1994 | Flynn et al. |
| 5,403,856 A | 4/1995 | Henning et al. |
| 5,430,145 A | 7/1995 | Flynn et al. |
| 5,442,008 A | 8/1995 | Fulberth et al. |
| 5,461,039 A | 10/1995 | Tschollar et al. |
| 5,470,975 A | 11/1995 | Atwal |
| 5,500,434 A | 3/1996 | Becker et al. |
| 5,502,199 A | 3/1996 | Angerbauer et al. |
| 5,504,080 A | 4/1996 | Karanewsky |
| 5,506,361 A | 4/1996 | Koh et al. |
| 5,508,272 A | 4/1996 | Robl |
| 5,525,723 A | 6/1996 | Robl |
| 5,552,397 A | 9/1996 | Karanewsky et al. |
| 5,554,624 A | 9/1996 | Almansa et al. |
| 5,554,625 A | 9/1996 | Rivero et al. |
| 5,593,971 A | 1/1997 | Tschollar et al. |
| 5,612,359 A | 3/1997 | Murugesan |
| 5,622,985 A | 4/1997 | Olukotun et al. |
| 5,656,603 A | 8/1997 | Simmons |
| 5,674,893 A | 10/1997 | Behounek et al. |
| 5,679,671 A | 10/1997 | Oinuma et al. |
| 5,684,016 A | 11/1997 | Henning et al. |
| 5,691,375 A | 11/1997 | Behounek et al. |
| 5,721,244 A | 2/1998 | Becker et al. |
| 5,733,558 A | 3/1998 | Breton et al. |
| 5,744,496 A | 4/1998 | Henning et al. |
| 5,747,504 A | 5/1998 | Henning et al. |
| 5,827,863 A | 10/1998 | Almansa et al. |
| 5,948,799 A | 9/1999 | Cropp |
| 5,952,305 A | 9/1999 | Pfeffer et al. |
| 5,972,990 A | 10/1999 | Pfeffer et al. |
| 5,977,160 A | 11/1999 | Pfeffer et al. |
| 6,180,660 B1 | 1/2001 | Whitney et al. |
| 2003/0158090 A1 | 8/2003 | Pedersen-Bjergaard et al. |
| 2005/0065203 A1 | 3/2005 | Yusuf |
| 2005/0101658 A1 | 5/2005 | Scholkens et al. |

FOREIGN PATENT DOCUMENTS

| | | |
|---|---|---|
| CA | 2026686 | 5/1991 |
| CA | 2117782 | 10/1993 |
| CA | 2 382 387 | 3/2001 |
| CA | 2 382 549 | 3/2001 |
| DE | 4308504 | 9/1994 |
| DE | 199 13 528 A1 | 6/2000 |
| EP | 0 079 022 | 5/1983 |
| EP | 0 158 927 B1 | 10/1985 |
| EP | 0 241 201 | 10/1987 |
| EP | 0 292 923 | 11/1988 |
| EP | 0 331 014 | 9/1989 |
| EP | 0 363 934 B1 | 4/1990 |
| EP | 0 401 705 A2 | 12/1990 |
| EP | 0 426 066 A2 | 5/1991 |
| EP | 0 457 514 A1 | 11/1991 |
| EP | 0 459 453 A2 | 12/1991 |
| EP | 0 461 548 A2 | 12/1991 |
| EP | 0 474 438 A1 | 3/1992 |
| EP | 0 481 522 B1 | 4/1992 |
| EP | 0 482 498 A2 | 4/1992 |
| EP | 0 508 665 A2 | 10/1992 |
| EP | 0 534 396 B1 | 3/1993 |
| EP | 0 534 492 B1 | 3/1993 |
| EP | 0 540 209 A1 | 5/1993 |
| EP | 0 547 442 A1 | 6/1993 |
| EP | 0 671 170 A1 | 9/1995 |
| EP | 0 671 171 A1 | 9/1995 |
| EP | 0 671 172 A1 | 9/1995 |
| EP | 0 738 510 A2 | 10/1996 |
| EP | 0 738 512 A1 | 10/1996 |
| EP | 0 747 050 A1 | 12/1996 |
| EP | 0 795 327 A1 | 9/1997 |
| EP | 0 317 878 B1 | 5/1999 |
| EP | 1 216 038 B1 | 9/2005 |
| GB | 2 171 103 A | 8/1986 |
| GB | 2 308 064 | 6/1997 |
| JP | 10081633 | 3/1998 |
| KR | 1996-7005549 | 11/1996 |
| SE | 9903028-0 | 8/2000 |
| WO | WO 90/05531 | 5/1990 |
| WO | WO 92/10188 | 6/1992 |
| WO | WO 92/19211 | 11/1992 |
| WO | WO 92/20673 | 11/1992 |
| WO | WO 93/17685 | 9/1993 |
| WO | WO 93/20839 | 10/1993 |
| WO | WO 94/07492 | 4/1994 |
| WO | WO 94/11369 | 5/1994 |
| WO | WO 95/13063 | 5/1995 |
| WO | WO/96/07400 | 8/1995 |
| WO | WO 95/26188 | 10/1995 |
| WO | WO 96/07400 A1 | 3/1996 |
| WO | WO 96/24373 | 8/1996 |
| WO | WO 96/40258 | 12/1996 |
| WO | WO 97/27745 | 8/1997 |
| WO | WO 97/49392 | 12/1997 |
| WO | WO 98/30216 | 7/1998 |
| WO | WO 99/09967 | 3/1999 |
| WO | WO 99/11260 | 3/1999 |
| WO | WO 99/20260 | 4/1999 |
| WO | WO 99/44590 | 9/1999 |
| WO | WO 00/02543 | 1/2000 |
| WO | WO 00/18395 | 4/2000 |
| WO | WO 00/45818 | 8/2000 |
| WO | WO 00/67737 | 11/2000 |
| WO | WO 00/71751 A1 | 11/2000 |
| WO | WO 01/11038 A2 | 2/2001 |
| WO | WO 01/15673 A2 | 3/2001 |
| WO | WO 01/15674 A2 | 3/2001 |
| WO | WO 01/15744 A1 | 3/2001 |
| WO | WO 01/76573 A2 | 10/2001 |
| WO | WO 01/76632 A1 | 10/2001 |
| WO | WO 01/78747 | 10/2001 |

OTHER PUBLICATIONS

Clairmont, "Heart Doc Loses Hope $11M Research Project Ends Early," Hamilton Spectator newspaper, p. A3, providing a date of May 1999.

Heart Outcomes Prevention Evaluation Study Investigators, "Effects of an Angiotensin-converting-enzyme inhibitor, Ramipril, on cardiovascular events in high-risk patients," The New England Journal of Medicine, vol. 342, No. 3, pp. 145-153 (2000).

Jeffrey, "New HOPE in heart study," Medical Post, vol. 35, No. 20, p. 1 (May 1999).

Morrison, Heart Drug Called Major Discovery Ramipril Better Than Aspirin, Fewer Side Effects, Hamilton Spectator newspaper, p. A7, providing a date of May 1999.

News Release, "Hope Study Indicates Ramipril Could Save One Million Lives Each Year", distributed by PR Newswire Europe Ltd. on behalf of McMaster University health Sciences, providing a date of May 1999.

Leslie Papp, "Aborted vitamin E study will be given second look," Toronto Star newspaper, p. A5 (May 1999).

Leslie Papp, "Researchers call off $11-million heart study," published in the Toronto Star newspaper, p. A5 (1999).

Opposition of Biogaran to European Patent No. 1 216 038, dated Jan. 17, 2006.

Opposition of Teva Pharmaceutical Industries, Ltd. to European Patent No. 1 216 038, dated Jun. 5, 2006.

Opposition of Hexal AG to European Patent No. 1 216 038, dated Jun. 2, 2006.

Opposition of Boehringer Ingelheim Pharma GmbH & Co. to European Patent No. 1 216 038, dated Jun. 2, 2006.
Opposition of Egis Gyogyszergyar to European Patent No. 1 216 038, dated Jun. 7, 2006.
Remme, "Bradykinin-Mediated Cardiovascular Protective Actions of ACE Inhibitors—A New Dimension in Anti-Ischaemic Therapy?," Drugs, vol. 54, Supp. 5, pp. 59-70 (1997).
Extract from website of World Health Organization, printed Feb. 21, 2006, (http://www.who/int/cardiovascular_diseases/en/cvd_atlas_03_risk_factors.pdf).
Danchin et al., "Angiotensin-Converting Enzyme Inhibitors in Patients With Coronary Artery Disease and Absence of Heart Failure or Left Ventricular Systolic Dysfuntion," Arch Intern Med, vol. 166, pp. 787-796 (2006).
Bail et al., "Who should be treated with angiotensin-converting enzyme inhibitors after myocardial infarction?," American Heart Journal, vol. 132, No. 1, part 2, pp. 244-250 (1996).
Johnson et al., "Angiotensin-Converting Enzyme Inhibitor Therapy Affects Left Ventricular Mass in Patients With Ejection Fraction >40% After Acute Myocardial Infarction," JACC, vol. 29, No. 1, pp. 49-54 (1997).
Domanski et al., "Effect of Angiotensin Converting Enzyme Inhibition on Sudden Cardiac Death in Patients Following Acute Myocardial Infarction," Journal of the American College of Cardiology, vol. 33, No. 3, pp. 598-604 (1999).
Linz et al., "Late Treatment With Ramipril Increases Survival in Old Spontaneously Hypertensive Rats," Hypertension, vol. 34, No. 2, pp. 291-295 (1999).
Zimmermann et al., "Effect of Long-term ACE Inhibition on Myocardial Tissue in Hypertensive Stroke-prone Rats," J. Mol Cell Cardiol, vol. 31, pp. 1447-1456 (1999).
U.S. Appl. No. 09/645,556, filed Aug. 25, 2000, Scholkens et al.
U.S. Appl. No. 11/415,137, filed May 2, 2006, Scholkens et al.
Office Action dated Jun. 20, 2001, during prosecution of U.S. Appl. No. 09/645,556.
Office Action dated Jul. 29, 2002, during prosecution of U.S. Appl. No. 09/645,556.
Office Action dated Apr. 9, 2003, during prosecution of U.S. Appl. No. 09/645,556.
Office Action dated Jul. 27, 2004, during prosecution of U.S. Appl. No. 09/645,556.
Office Action dated Nov. 3, 2004, during prosecution of U.S. Appl. No. 09/645,556.
Office Action dated Jan. 24, 2005, during prosecution of U.S. Appl. No. 09/645,556.
Office Action dated Feb. 24, 2005, during prosecution of U.S. Appl. No. 09/645,556.
Office Action dated Jun. 29, 2005, during prosecution of U.S. Appl. No. 09/645,556.
Office Action dated Nov. 3, 2005, during prosecution of U.S. Appl. No. 09/645,556.
Aberg et al., "Effects of Captopril on Atherosclerosis in Cynomolgus Monkeys," Journal of Cardiovascular Pharmacology, vol. 15 (suppl. 5), pp. S65-S72 (1990).
Abstract From the 65th Scientific Sessions, Circulation, vol. 86 (4 Suppl. 1), p. I-53, Abstracts 0207-0210 (1992).
Acute Infarction Ramipril Efficacy (AIRE) Study Investigators, "Effect of ramipril on mortality and morbidity of survivors of acute myocardial infarction with clinical evidence of heart failure," The Lancet, vol. 342, pp. 821-828 (1993).
Alderman et al., "Association of the Renin-Sodium Profile with the Risk of Myocardial Infarction in Patients with Hypertension," The New England Journal of Medicine, vol. 324, No. 16, pp. 1098-1104 (1991).
Allen et al., "Diabetic Vascular Hypertrophy and Albuminuria: Effect of Angiotensin Converting Enzyme Inhibition," Journal of Diabetes and its Complications, vol. 9, pp. 318-322 (1995).
Anderson et al., "Therapeutic Advantage of Converting Enzyme Inhibitors in Arresting Progressive Renal Disease Associated with Systemic Hypertension in the Rat," J. Clin. Invest., vol. 77, pp. 1993-2000 (1986).
Antiplatelet Trialists' Collaboration, "Collaborative overview of randomised trials of antiplatelet therapy—I: Prevention of death, myocardial infarction, and stroke by prolonged antiplatelet therapy in various categories of patients," BMJ, vol. 308, pp. 81-106 (1994).
Aronow, "Treatment of Congestive Heart Failure in Older Persons," JAGS, vol. 45, No. 10, pp. 1252-1258 (1997).
Avezum et al., "Pharmacological Treatment for Myocardial Infarction Part 2: Implications of Clinical Trials of Other Adjunctive Therapies," Indian Heart J., vol. 47, pp. 95-105 (1995).
Avezum et al., "Recent Advances and Future Directions in Myocardial Infarction," Cardiology, vol. 84, pp. 391-407 (1994).
Balabolkin, "Endocrinology," Universum Publishing, pp. 390-391 (1988), with English language translation of portion of text.
Bangdiwala et al., "Studies of Left Ventricular Dysfunction (SOLVD) Registry: Rationale, Design, Methods and Description of Baseline Characteristics," The American Journal of Cardiology, vol. 70, No. 33, pp. 347-353 (1992).
Basis of Internal Medicine, 4th Edition, Edited by Chen Haozhu, Peoples Medical Publishing House, pp. 226, 227, 230, 232, 238, 242, and 243 (1996), and partial translation.
Bauer et al., "An open multicenter study to assess the long-term efficacy, tolerance, and safety of the oral angiotensin converting enzyme inhibitor ramipril in patients with mild to moderate essential hypertension," J Cardiovasc Pharmacol., vol. 13 (suppl. 3), pp. S70-S74 (1989).
Becker et al., "Loop diuretics combined with an ACE inhibitor for treatment of hypertension: a study with furosemide, piretanide, and ramipril in spontaneously hypertensive rats," J Cardiovasc Pharmacol., vol. 13 (suppl. 3), pp. S 35-S 39 (1989).
Becker et al., "Ramipril: review of pharmacology," Am. J Cardiol., vol. 59, No. 10, pp. 3D-11D (1987).
Benedict et al., "Comparative Neurohormonal Responses in Patients with Preserved and Impaired Left Ventricular Ejection Fraction: Results of the Studies of Left Ventricular Dysfunction (SOLVD) Registry," JACC, vol. 22 (4 suppl. A), pp. 146A-153A (1993).
Berkow et al., the Merck Manual (Home Ed.) p. 93 (1997).
Björck et al, "Renal protective effect of enalapril in diabetic nephropathy," BMJ, vol. 304, pp. 339-343 (1992).
Björck et al., "Beneficial effects of angiotensin converting enzyme inhibition on renal function in patients with diabetic nephropathy," BMJ, vol. 293, pp. 471-774 (1986).
Blumenthal, "Treatment of Congestive Heart Failure, Experience With Fosinopril," American Journal of Hypertension, Ltd., vol. 10, No. 10, Part 2, pp. 289S-298S (1997).
Bohannon, "Coronary artery disease and diabetes," Postgraduate Medicine, vol. 105, No. 2, pp. 66-68, 71-72, and 77-80 (1999).
Bohm et al., "Studies on the antihypertensive effect of single doses of the angiotensin converting enzyme inhibitor ramipril (HOE 498) in man," Eur J Clin Pharmacol., vol. 30, No. 5, pp. 541-547 (1986).
Borghi et al., "Evidence-Based Medicine and ACE Inhibition," Journal of Cardiovascular Pharmacology, vol. 32 (suppl. 2), pp. S24-S-35 (1998).
Bouthier et al., "Cardiac hypertrophy and arterial distensibility in essential hypertension," Am. Heart J., vol. 109, No. 6, pp. 1345-1352 (1985).
Braunwald, Ed., "Heart Disease: A Textbook of Cardiovascular Medicine," vol. 1, Chapter 15, "Clinical Aspects of Heart Failure: High-Output Heart Failure; Pulmonary Edema," W.B. Saunders Company, pp. 445-470 (1997).
Brown et al., "Angiotensin-Converting Enzyme Inhibitors," Circulation, vol. 97, pp. 1411-1420 (1998).
Brown et al., "Selective Stimulation of Tissue-Type Plasminogen Activator (t-PA) In Vivo by Infusion of Bradykinin," Thrombosis and Haemostatis, vol. 77, No. 3, pp. 522-525 (1997).
Brunner et al., "Essential Hypertension: Renin and Aldosterone, Heart Attack and Stroke," The New England Journal of Medicine, vol. 286, No. 9, pp. 441-449 (1972).
Bussien et al., "The Effect of the conveying enzyme inhibitor HOE-498 ramipril on the renin-angiotensin system of normal volunteers," Naunyn-Schmiedeberg's Archives of Pharmacology, vol. 329, pp. 3-69 (1985).
Cairns et al., "ISIS-3: a randomised comparison of streptokinase vs tissue plasminogen activator vs anistreplase and of aspirin plus heparin vs aspirin alone among 41 299 cases of suspected acute myocardial infarction," The Lancet, vol. 339, No. 8796, pp. 753-770 (1992).

Cambien et al., "Deletion polymorphism in the gene for angiotensin-converting enzyme is a potent risk factor for myocardial infarction," Nature, vol. 359, pp. 641-644 (1992).

Campbell-Boswell et al., "Effects of Angiotensin II and Vasopressin on Human Smooth Muscle Cells in Vitro[1]," Experimental and Molecular Pathology, vol. 35, pp. 265-276 (1981).

Canner et al., "Fifteen Year Mortality in Coronary Drug Project Patients: Long-Term Benefit With Niacin," JACC, vol. 8, No. 6, pp. 1245-1255 (1986).

Cashin-Hemphill et al., "Angiotensin-Converting Enzyme Inhibition as Antiatherosclerotic Therapy: No Answer Yet," Am. J. Cardiol., vol. 83, pp. 43-47 (1999).

Chobanian et al., "Antiatherogenic Effect of Captopril in the Watanabe Heritable Hyperlipidemic Rabbit," Hypertension, vol. 15, pp. 327-331 (1990).

Chobanian, "The Effects of ACE Inhibitors and Other Antohypertensive Drugs on Cardiovascular Risk Factors and Atherogenesis," Clin. Cardio., vol. 13, pp. VII-43-48 (1990).

Clarke et al., "Underestimation of Risk Associations Due to Regression Dilution in Long-term Follow-up of Prospective Studies," Am. Journal of Epidemiology, vol. 150, No. 4, pp. 341-353 (1999).

Collins et al., "Blood pressure, stroke, and coronary heart disease," The Lancet, vol. 335, pp. 827-838 (1990).

Consensus Trial Study Group, "Effects of Enalapril on Mortality in Severe Congestive Heart Failure," The New England Journal of Medicine, vol. 316, No. 23, pp. 1429-1435 (1987).

Daemen et al.,"Angiotensin II Induces Smooth Muscle Cell Proliferation in the Normal and Injured Rat Arterial Wall," Circulation Research, vol. 68, No. 2, pp. 450-456 (1991).

Database WPI, Week 19944, Derwent Publications Ltd., London, GB, AN 199-520858, XP-002166044, Masuda Yoshinobu, Honda Yayoi, Minato Hisao: "Inhibitor of cerebral vasospasm", date not provided.

de Leeuw et al.,"Preliminary experiences with HOE 498, a novel long-acting converting enzyme inhibitor, in hypertensive patients," J Cardiovasc Pharmacol., vol. 7, No. 6, pp. 1161-1165 (1985).

de Leeuw et al., "Short- and long-term effects of ramipril in hypertension," Am J Cardiol., vol. 59, No. 10, pp. 79D-82D (1987).

Deckert et al., "Microalbuminuria," Diabetes Care, vol. 15, No. 9, pp. 1181-1191 (1992).

Deng et al., "Proinflammatorische Zytokine und kardiale Pumpfunktion," Z. Kardiol, vol. 86, pp. 788-802 (1997).

"Diabetes and Hypertension: Experimental Models," Clin. Exp. Hypertens, vol. 21, pp. 5-6 (1999).

Donahue et al.,"Diabetes Mellitus and Macrovascular Complications," Diabetes Care, vol. 15, No. 9, pp. 1141-1155 (1992).

Donnelly, "Angiotensin-Converting Enzyme Inhibitors and Insulin Sensitivity: Metabolic Effects in Hypertension, Diabetes and Heart Failure," Journal of Cardiovascular Pharmacology, vol. 20 (suppl. 11), pp. S38-S44 (1992).

Dunn et al., "Enalapril Improves Systemic and Renal Hemodynamics and Allows Regression of Left Ventricular Mass in Essential Hypertension," Am. J. Cardiol, vol. 53, pp. 105-108 (1984).

Durrington, "Diabetic dyslipidaemia," Bailliere's Clinical Endocrinology and Metabolism, vol. 13, No. 2, pp. 265-278 (1999).

Dzau, "Angiotensin converting enzyme inhibitors and the cardiovascular system," Journal of Hypertension, vol. 10 (suppl. 3), pp. S3-S10 (1992).

Dzau, "Cardiac Renin-Angiotensin System," The American Journal of Medicine, vol. 84 (suppl. 3A), pp. 22-27 (1988).

Dzau, "Clinical implications for therapy: possible cardioprotective effects of ACE inhibition," Br J Clin Pharmac., vol. 28, pp. 183S-187S (1989).

Eberhardt et al., "Angiotensin II Receptor Blockade: An Innovative Approach to Cardiovascular Pharmacotherapy," J. Clin. Pharmacol, vol. 33, pp. 1023-1038 (1993).

Editorial, "Angiotensin II: Hemodynamic Regulator or Growth Factor?," J. Mol Cell Cardiol, vol. 22, pp. 739-747 (1990).

Engeli et al., "Co-expression of renin-angiotensin system genes in human adipose tissue," Journal of Hypertension, vol. 17, No. 4, pp. 555-560 (1999).

Estacio et al., "Antihypertensive Therapy in Type 2 Diabetes: Implications of the Appropriate Blood Pressure Control in Diabetes (ABCD) Trial," American Journal of Cardiology, vol. 82, No. 9B, pp. 9R-14R (1998).

ETDRS Investigators, "Aspirin Effects on Mortality and Morbidity in Patients With Diabetes Mellitus," JAMA, vol. 268, No. 10, pp. 1292-1300 (1992).

EURopean trial On reduction of cardiac events with Perindopril in stable coronary Artery disease Investigators, Efficacy of perindopril in reduction of cardovascular events among patients with stable coronary artery disease: randomised, double-blind, placebo-controlled, multicentre trial (the Europa study), The Lancet, vol. 362, pp. 782-788 (2003).

FDA Orange Book Active Ingredient Detail Record Search, printed on Jun. 8, 2001.

Fogo et al., "Importance of angiogenic action of angiotensin II in the glomerular growth of maturing kidneys," Kidney International, vol. 38, pp. 1068-1074 (1990).

Francis et al., "Comparison of Neuroendocrine Activation in Patients With Left Ventricular Dysfunction With and Without Congestive Heart Failure," Circulation, vol. 82, pp. 1724-1729 (1990).

Fukiyama et al.,"Efficacy and safety of ramipril (HOE 498) in the treatment of hypertension: dose finding study," Am J Cardiol., vol. 59, No. 10, pp. 121D-124D (1987).

Garg et al., "Overview of Randomized Trials of Angiotensin-Converting Enzyme Inhibitors on Mortality and Morbidity in Patients With Heart Failure," JAMA, vol. 273, No. 18, pp. 1450-1456 (1995).

Geisterfer et al., "Angiotensin II Induces Hypertrophy, not Hyperplasia, of Cultured Rat Aortic Smooth Muscle Cells," Circulation Research, vol. 62, No. 4, pp. 749-756 (1988).

Gerstein et al., "Rationale and Design of a Large Study to Evaluate the Renal and Cardiovascular Effects of an ACE Inhibitor and Vitamin E in High-Risk Patients With Diabetes," Diabetes Care, vol. 19, No. 11, pp. 1225-1228 (1996).

Gey et al.,"Inverse correlation between plasma vitamin E and mortality from ischemic heart disease in cross-cultural epidemiology," Am J Clin Nutr., vol. 53 (suppl. 1), pp. S326-S334 (1991).

Gisen Group, "Randomised placebo-controlled trial of effect of ramipril on decline in glomerular filtration rate and risk of terminal renal failure in proteinuric, non-diabetic nephropathy," The Lancet, vol. 349, pp. 1857-1863 (1997).

Goldman et al., "Saphenous Vein Graft Patency 1 Year After Coronary Artery Bypass Surgery and Effects of Antiplatelet Therapy," Circulation, vol. 80, pp. 1190-1197 (1989).

Guidelines Subcommittee, "1999 World Health Organization—International Society of Hypertension Guidelines for the Management of Hypertension," Journal of Hypertension, vol. 17, No. 2, pp. 151-183 (1999).

Hall et al., "Captopril Slows the Progression of Chronic Renal Disease in Partially Nephrectomized Rats," Toxicology and Applied Pharmacology, vol. 80, pp. 517-526 (1985).

Hall et al., "Follow-up study of patients randomly allocated ramipril or placebo for heart failure after acute myocardial infarction: Aire Extension (AIREX) Study," The Lancet, vol. 349, pp. 1493-1497 (1997).

Hansson et al., "Effect of angiotensin-converting-enzyme inhibition compared with conventional therapy on cardiovascular morbidity and mortality in hypertension: the Captopril Prevention Project (CAPPP) randomised trial," The Lancet, vol. 353, pp. 611-616 (1999).

Hansson et al., "Effects of intensive blood-pressure lowering and low-dose aspirin in patients with hypertension: principal results of the Hypertension Optimal Treatment (HOT) randomised trial," The Lancet, vol. 351, pp. 1755-1762 (1998).

Hansson, "The Hypertension Optimal Treatment study and the importance of lowering blood pressure," Journal of Hypertension, vol. 17 (suppl. 1), pp. S9-S13 (1999).

Hayek et al., "Effect of Angiotensin Converting Enzyme Inhibitors on LDL Lipid Peroxidation and Atherosclerosis Progression in Apo E Deficient Mice," Circulation, vol. 92, No. 8, p. I-625 (1995).

Heber et al., "First dose response and 24-hour antihypertensive efficacy of the new once-daily angiotensin converting enzyme inhibitor, ramipril," Am J Cardiol., vol. 62, No. 4, pp. 239-245 (1988).

Heeg et al, "Reduction of proteinuria by angiotensin converting enzyme inhibition," Kidney International, vol. 32, pp. 78-83 (1987).

Holmes et al., "Long-term Outcome of Patients With Depressed Left Ventricular Function Undergoing Percutaneous Transluminal Coronay Angioplasty," Circulation, vol. 87, No. 1, pp. 21-29 (1993).

Hommel et al., "Effect of captopril on kidney function in insulin-dependent diabetic patients with nephropathy," BMJ, vol. 293, pp. 467-470 (1986).

Hsueh, "In diabetes, treat hidden heart disease," Cleveland Clinic Journal of Medicine, vol. 67, No. 11, pp. 807-813 (2000).

Ichikawa et al., "Glomerular Actions of Angiotensin II," The American Journal of Medicine, pp. 43-49 (1984).

Ip et al., "Syndromes of Accelerated Atherosclerosis: Role of Vascular Injury And Smooth Muscle Cell Proliferation," JACC, vol. 15, No. 7, pp. 1667-1687 (1990).

Izumo et al., "Protooncogene induction and reprogramming of cardiac gene expression produced by pressure overload," Proc. Natl. Acad. Sci. USA, vol. 85, pp. 339-343 (1988).

JACC, vol. 19, No. 3, abstracts 207A, Nos. 768-3, 768-4, 768-5, and 768-6 (1992).

Kaneko et al., "Effect of ramipril, a new angiotensin converting enzyme inhibitor, on diurnal variations of blood pressure in essential hypertension," Am J Cardiol., vol. 59, No. 10, pp. 86D-91D (1987).

Kannel, "Left ventricular hypertrophy as a risk factor: the Framingham experience," Journal of Hypertension, vol. 9 (suppl. 2), pp. 53-59 (1991).

Karlberg et al., "Efficacy, tolerance and hormonal effects of a new oral angiotensin converting enzyme inhibitor, ramipril (HOE 498), in mild to moderate primary hypertension," Am J Cardiol., vol. 59, No. 10, pp. 104D-109D (1987).

Kasiske et al., "Effect of Antihypertensive Therapy on the Kidney in Patients with Diabetes: A Meta-Regression Analysis," Annals of Internal Medicine, vol. 118, pp. 129-138 (1993).

Keane et al., "Renal Protective Effects of Angiotensin-Converting Enzyme Inhibition," The American Journal of Cardiology, vol. 65, pp. 49I-53I (1990).

Keys, "A Multivariate Analysis of Death and Coronary Heart Disease," Seven Countries, pp. 1-381 Harvard University Press (1980).

Kindler et al., "Therapeutic efficacy and tolerance of ramipril in hypertensive patients with renal failure," J Cardiovasc Pharmacol., vol. 13 (suppl. 3), pp. S55-S58 (1989).

Kleber, "Socioeconomic Aspects of ACE Inhibition in the Secondary Prevention in Cardiovascular Diseases," American Journal of Hypertension, vol. 7, No. 9, pp. 112S-116S (1994).

Kreisberg, "Diabetic Dyslipidemia," American Journal of Cardiology, vol. 82, No. 12A, pp. 67U-73U (1998).

Lacourciere et al.,"Captopril or conventional therapy in hypertensive type II diabetics," Hypertension, vol. 21, pp. 786-794 (1993).

Law, "Lipids and cardiovascular disease," Evidence Based Cardiology, BMJ Books, pp. 191-205 (1998).

Lee et al., "Effects of perindopril on hypertension and stroke prevention in experimental animals," Can. J. Cardiol., vol. 10 (suppl. D), pp. 33D-36D (1994).

Lefer et al., "Cardioprotective Effects of Enalapril in Acute Myocardial Ischemia," Pharmacology, vol. 29, pp. 61-69 (1984).

Leor, et al., "Aspirin and Mortality in Patients Treated With Angiotensin-Converting Enzyme Inhibitors," Journal of the American College of Cardiology, vol. 33, No. 7, pp. 1920-1925 (1999).

Lever, "Angiotensin II, Angiotensin-Converting Enzyme Inhibitors and Blood Vessel Structure," The American Journal of Medicine, vol. 92 (suppl. 4B), pp. 35 S-38 S (1992).

Lewis et al., "The effect of angiotensin-converting-enzyme inhibition on diabetic nephropathy," The New England Journal of Medicine, vol. 329, No. 20, pp. 1456-1462 (1993).

Lindholm et al., "The Swedish Trial in Old Patients with Hypertension-2 (STOP-Hypertension-2): A Progress Report," Blood Pressure, vol. 5, pp. 300-304 (1996).

Linz et al., "Long-term ACE Inhibition Doubles Lifespan of Hypertensive Rats," Circulation, vol. 96, No. 9, pp. 3164-3172 (1997).

Lonn et al.,"Emerging approaches in preventing cardiovascular disease," British Medical Journal, vol. 318, pp. 1337-1341 (1999).

Lonn et al., "Emerging Role of Angiotensin-Converting Enzyme Inhibitors in Cardiac and Vascular Protection," Circulation, vol. 90, No. 4, pp. 2056-2069 (1994).

Lonn et al.; "Study Design and Baseline Characteristics of the Study to Evaluate Carotid Ultrasound Changes in Patients Treated With *Ramipril* and Vitamin E: Secure," Am. J. Cardial, vol. 78, pp. 914-919 (1996).

Lüscher, "Angiotensin, ACE inhibitors and endothelial control of vasomotor tone," Basic Res Cardiol., vol. 88 (suppl. 1), pp. 15-24 (1993).

MacMahon et al., "Blood pressure, stroke, and coronary heart disease," The Lancet, vol. 335, pp. 765-774 (1990).

Mak et al., "Protective effects of sulfhydryl-containing angiotensin converting enzyme inhibitors against free radical injury in endothelial cells," Biochemical Pharmacology, vol. 40, No. 9, pp. 2169-2175 (1990).

Mancini et al., "Angiotensin-Converting Enzyme Inhibition with Quinapril Improves Endothelial Vasomotor Dysfunction in Patients with Coronary Artery Disease—the TREND (Trial on Reversing Endothelial Dysfunction) Study," Circulation, vol. 94, No. 3, pp. 258-265 (1996).

Mann et al., "Basic Mechanisms in Congestive Heart Failure," Chest, vol. 105, No. 3, pp. 897-904 (1994).

Marre et al, "Converting enzyme inhibition and kidney function in normotensive diabetic patients with persistent microalbuminuria," BMJ, vol. 294, pp. 1448-1452 (1987).

Marre et al., "Prevention of diabetic nephropathy with enalapril in normotensive diabetics with microalbuminuria," BMJ, vol. 297, pp. 1092-1095 (1988).

Martin et al., "Serum Cholesterol, Blood Pressure, and Mortality: Implications from a Cohort of 361 662 Men," The Lancet, pp. 933-936 (1986).

Martindale, "The Complete Drug Reference," Parfitt Ed., Thirty-second Edition, pp. 836, 865, 891-892, 899, 951, and 960, Pharmaceutical Press, London, U.K. (1999).

Martindale, The Extra Pharmacopoeia, pp. 863, 864, 899, 900, 940, and 941, Royal Pharmaceutical Society, London (1996).

Mathiesen et al., "Efficacy of captopril in postponing nephropathy in normotensive insulin dependent diabetic patients with microalbuminuria," BMJ, vol. 303, No. 7, pp. 81-87 (1991).

Matsumori, "The use of cytokine inhibitors A new therapeutic insight into heart failure," Int. Journal of Cardiology, vol. 62 (suppl. 1), pp. S3-S12 (1997).

McKelvie et al., "Role of angiotensin converting enzyme inhibitors in patients with left ventricular dysfunction and congestive heart failure," Eur. Heart J., vol. 15 (suppl. B), pp. 9-13 (1994).

Meade et al., "The epidemiology of plasma renin," Clinical Science, vol. 64, pp. 273-280 (1983).

Merck Index, 12th Ed., pp. 1394-1395 (1996).

Merck Manual, 14th Ed., by Merck & Co., Inc. (NJ) pp. 488-489 (1982).

Metelitsa, "Handbook on Clinical Pharmacology of Cardiovascular Medicaments," Medpraktika, pp. 619 and 272 (1996), with English language translation of portion of text.

Mujais et al., "Reversal of Left Ventricular Hypertrophy with Captopril: Heterogeneity of Response Among Hypertensive Patients," Clin. Cardiol., vol. 6, pp. 595-602 (1983).

Naftilan et al., "Angiotensin II Induces *c-fos* Expression in Smooth Muscle Via Transcriptional Control," Hypertension, vol. 13, pp. 706-711 (1989).

Naftilan et al., "Induction of Platelet-derived Growth Factor A-chain and *c-myc* Gene Expressions by Angiotensin II in Cultured Rat Vascular Smooth Muscle Cells," J. Clin. Invest., vol. 83, pp. 1419-1424 (1989).

Nakamura et al., "Chronic Administration of Angiotensin II Receptor Antagonist, TCV-116, In Cardiomyopathic Hamsters," American Physiological Society, pp. 2297-2304 (1994).

Neil et al., "A Prospective Population-Based Study of Microalbuminuria as a Predictor of Mortality in NIDDM," Diabetes Care, vol. 16, No. 7, pp. 996-1003 (1993).

Nicoletti et al., "Cardiac fibrosis and inflammation: interaction with hemodynamic and hormonal factors," Cardiovascular Research, vol. 41, pp. 532-543 (1999).

Ning et al., "Secondary prevention of cardiac events following myocardial infarction: effects of atenolol and enalapril," Chinese Medical Journal, vol. 110, No. 8, pp. 602-606 (1997).

Noth et al., "Diabetic Nephrophathy: Hemodynamic Basis and Implications for Disease Management," Annals of Internal Medicine, vol. 110, No. 10, pp. 795-813 (1989).

Ogiku et al., "Prophylactic Effect of Imidapril on Stroke in Stroke-Prone Spontaneously Hypertensive Rats," Stroke, vol. 24, No. 2, pp. 245-252 (1993).

Opie, "Principles of Combination Therapy for Hypertension: What We Learn from the HOT and Other Studies—A Personal Point of View," Cardiovascular Drugs and Therapy, vol. 12, No. 5, pp. 425-429 (1998).

Pahor et al., "New Evidence on the Prevention of Cardiovascular Events in Hypertensive Patients with Type 2 Diabetes," Journal of Cardiovascular Pharmacology, vol. 32 (suppl. 2), pp. S18-S23 (1998).

Parving et al., "Effect of captopril on blood pressure and kidney function in normotensive insulin dependent diabetics with nephropathy," BMJ, vol. 299, pp. 533-536 (1989).

Parving et al., "Prevalence and causes of albuminuria in non-insulin-dependent diabetic patients," Kidney International, vol. 41, pp. 758-762 (1992).

Parving et al., "Protection of kidney function and decrease in albuminuria by captopril in insulin dependent diabetics with nephropathy," BMJ, vol. 297, pp. 1086-1091 (1988).

Patent File History of Canadian Patent No. 2,382,387, date unavailable.

Patent File History of Canadian Patent No. 2,383,549, date unavailable.

Patten et al., "Acute and long-term effects of the angiotensin-converting enzyme inhibitor, enalapril, on adrenengic activity and sensitivity during exercise in patients with left ventricular systolic dysfunction," Am. Heart J., vol. 134, pp. 37-43 (1997).

PEACE Trial Investigators, "Angiotensin-Converting-Enzyme Inhibition in Stable Coronary Artery Disease," N Engl J Med, vol. 351, No. 20, pp. 2058-2068 (2004).

Pepine, "Ongoing Clinical Trials of Angiotensin-Converting Enzyme Inhibitors for Treatment of Coronary Artery Disease in Patients with Preserved Left Ventricular Function," JACC, vol. 27, No. 5, pp. 1048-1052 (1996).

Pfeffer et al., "Effect of Captopril on Mortality and Morbidity in Patients with Left Ventricular Dysfunction after Myocardial Infarction," The New England Journal of Medicine, vol. 327, No. 10, pp. 669-677 (1992).

Pfeffer et al., "Effect of Captopril on progressive ventricular dilatation after anterior myocardial infarction," The New England Journal of Medicine, vol. 319, No. 2, pp. 80-86 (1988).

Pfeffer et al., "Survival after an experimental myocardial infarction: beneficial effects of long-term therapy with captopril," Circulation, vol. 72, No. 2, pp. 406-412 (1985).

Pfeffer, et al., "Prevention of Events With Angiotensin-Converting Enzyme Inhibition (The PEACE Study Design)," The American Journal of Cardiology, vol. 82, No. 3A, pp. 25H-30H (1998).

Pfeffer, et al., "The continuation of the Prevention of Events With Angiotensin-Converting Enzyme Inhibition (PEACE) Trial," American Heart Journal, vol. 142, No. 3, pp. 375-377 (2001).

Physician's Desk Reference, 53rd Ed., pp. 1293-1296 (1999).

Pitt et al., "The QUinapril Ischemic Event Trial (QUIET): Evaluation of Chronic ACE Inhibitor Therapy in Patients With Ischemic Heart Disease and Preserved Left Ventricular Function," The American Journal of Cardiology, vol. 87, pp. 1058-1063 (2001).

Pitt, "ACE Inhibitors for Patients with Vascular Disease without Left Ventricular Dysfunction-May They Rest in PEACE?," N Engl J Med, vol. 351, No. 20, pp. 2115-2117 (2004).

Powell et al., "Inhibitors of Angiotensin-Converting Enzyme Prevent Myointimal Proliferation After Vascular Injury," Science, vol. 245, pp. 186-188 (1989).

Predel et al., "Combined treatment of severe essential hypertension with the new angiotensin converting enzyme inhibitor ramipril," Am J Cardiol., vol. 59, No. 10, pp. 143D-148D (1987).

Ravid et al., "Long-term Renoprotective Effect of Angiotensin-converting Enzyme Inhibition in Non-insulin-dependent Diabetes Mellitus," Archives of Internal Medicine, vol. 156, No. 3, pp. 286-289 (1996).

Ravid et al., "Long-Term Stabilizing Effect of Angiotensin-Converting Enzyme Inhibition on Plasma Creatinine and on Proteinuria in Normotensive Type II Diabetic Patients," Annals of Internal Medicine, vol. 118, No. 8, pp. 577-581 (1993).

Re, "The Cellular Biology of Angiotensin: Paracrine, Autocrine and Intracrine Actions in Cardiovascular Tissues," J. Mol. Cell. Cardiol, vol. 21 (suppl. V), pp. 63-69 (1989).

Ridker et al., "Stimulation of Plasminogen Activator Inhibitor In Vivo by Infusion of Angiotensin II—Evidence of a Potential Interaction Between the Renin-Angiotensin System and Fibrinolytic Function," Circulation, vol. 87, No. 6, pp. 1969-1973 (1993).

Ross, "The Pathogenesis of Atherosclerosis—an update," The New England Journal of Medicine, vol. 314, No. 8, pp. 488-499 (1986).

Rowland, "Cardiology mapping new approaches to treatment," cnn.com, providing a date of Nov. 1999.

Ruggenenti et al., "Primary prevention of renal failure in diabetic patients: the Bergamo Nephrologic Diabetes Complication Trial," Journal of Hypertension, vol. 16 (suppl. 1), pp. S95-S97 (1998).

Ruggenenti et al., "Renal function and requirement for dialysis in chronic nephropathy patients on long-term ramipril: REIN follow-up trial," The Lancet, vol. 352, pp. 1252-1256 (1998).

Ruggenenti et al., "Renoprotective properties of ACE-inhibition in non-diabetic nephropathies with non-nephrotic proteinuria," The Lancet, vol. 354, pp. 359-364 (1999).

Rutherford et al., "Effects of Captopril on Ischemic Events After Myocardial Infarction: Results of the Survival And Ventricular Enlargement Trial," Circulation, vol. 90, pp. 1731-1738 (1994).

Sampson et al., "Regression of Left Ventricular Hypertrophy with 1 Year of Antihypertensive Treatment in Type 1 Diabetic Patients with Early Nephropathy" Diabetic Medicine, vol. 8, pp. 106-110 (1991).

Santoni et al., "Angiotensin converting enzyme inhibition, pulse wave velocity and ambulatory blood pressure measurement in essential hypertension," Clin. And Exper.-Theory and Practice, vol. A11 (suppl. 2), pp. 535-544 (1989).

Sasayama et al., "New insights into the pathophysiological role for cytokines in heart failure," Cardiovascular Research, vol. 42, pp. 557-564 (1999).

Savage et al., "Progressive Renal Insufficiency: The Role of Angiotensin Converting Enzyme Inhibitors," Advances in Internal Medicine, vol. 37, pp. 85-101 (1991).

Schieffer et al., "Expression of Angiotensin II and Interleukin 6 in Human Coronary Atherosclerotic Plaques," Circulation, vol. 101, pp. 1372-1378 (2000).

Schreiner et al., "Antihypertensive Efficacy, Tolerance, and Safety of Long-Term Treatment with Ramipril in Patients with Mild-to-Moderate Essential Hypertension," Journal of Cardiovascular Pharmacology, vol. 18 (suppl. 2), pp. S137-S140 (1991).

Schulz et al., "Cardiovascular Therapy: Evidence-based Medicine - Questions and Answers-," Table of Contents and Chapter F, "Post-myocardial infarction with poor LV function," medpharm GmbH Scientific Publishers, pp. 7-14 and 171-183 (2001).

Schunkert et al., "Pharmacokinetics of ramipril in hypertensive patients with renal insufficiency," Eur J Clin Pharmacol., vol. 37, No. 3, pp. 249-256 (1989).

Schwartz et al., "Pathogenesis of the Atherosclerotic Lesion," Diabetes Care, vol. 15, No. 9, pp. 1156-1167 (1992).

Serruys et al.,"Does the New Angiotensin Converting Enzyme Inhibitor Cilazapril Restenosis After Percutaneous Transluminal Coronary Angioplasty," Circulation, vol. 86, No. 1, pp. 100-110 (1992).

Sixth Report of the Joint National Committee on Prevention, Detection, Evaluation, and Treatment of High Blood Pressure (1997).

SOLVD Investigators, "Effect of enalapril on mortality and development of heart failure in asymptomatic patients with reduced left ventricular ejection fractions," The New England Journal of Medicine, vol. 327, No. 10, pp. 685-691 (1992).

SOLVD Investigators, "Effect of enalapril on survival in patients with reduced left ventricular ejection fractions and congestive heart failure," The New England Journal of Medicine, vol. 325, No. 5, pp. 293-302 (1991).

Stamler et al., "Diabetes, Other Risk Factors, and 12-Yr Cardiovascular Mortality for Men Screened in the Multiple Risk Factor Intervention Trial," Diabetes Care, vol. 16, No. 2, pp. 434-444 (1993).

Stein et al., "Drug Treatment of Hypertension in Patients With Diabetes Mellitus," Diabetes Care, vol. 14, No. 6, pp. 425-448 (1991).

Steinberg et al., "Modifications of Low-Density Lipoprotein That Increase Its Atherogenicity," The New England Journal of Medicine, vol. 320, No. 14, pp. 915-924 (1989).

Stier, Jr. et al., "Stroke Prevention by Losartan in Stroke-prone Spontaneously Hypertensive Rats," Journal of Hypertension, vol. 11 (suppl. 3), pp. S37-S42 (1993).

Stier, Jr., et al., "Enalapril Prevents Stroke and Kidney Dysfunction in Salt-Loaded Stroke-Prone Spontaneously Hypertensive Rats," Hypertension, vol. 13, No. 2, pp. 115-121 (1989).

Stumpe et al., "Effects of the new angiotensin-converting enzyme inhibitor, ramipril, in patients with essential hypertension," Klin Wochenschr, vol. 64, No. 12, pp. 558-562 (1986).

Swedberg et al., "Effects of the early administration of enalapril on mortality in patients with acute myocardial infarction," New England Journal of Medicine, vol. 327, No. 10, pp. 678-684 (1992).

Swynghedauw, "Molecular Mechanism of Myocardial Remodeling," Physiological Reviews, vol. 79, No. 1, pp. 215-262 (1999).

Taguma et al., "Effect of Captopril on Heavy Proteinuria in Azotemic Diabetics," The New England Journal of Medicine, vol. 313, No. 26, pp. 1617-1620 (1985).

Tatti, et al, "Outcome Results of the Fosinopril Versus Amlodipine Cardiovascular Events Randomized Trial (FACET) in Patients with Hypertension and NIDDM," Diabetes Care, vol. 21, No. 4, pp. 597-603 (1998).

Tochikubo et al., "Event of ramipril on 24-hour variability of blood pressure and heart rate in essential hypertension," Am J Cardiol., vol. 59, No. 10, pp. 83D-85D (1987).

Trenkwalder, "Effects of candesartan cilexetil on glucose homeostasis," Basic Res Cardiol, vol. 93 (suppl. 2), pp. 140-144 (1998).

Tsuyuki et al., "Combination neurohormonal blockade with ACE inhibitors, angiotensin II antagonists and beta-blockers in patients with congestive heart failure: Design of the Randomized Evaluation of Strategies for Left Ventricular Dysfunction (RESOLVD) Pilot Study," Can. J. Cardiol, vol. 13, No. 12, pp. 1166-1174 (1997).

Tu et al., "The striking effect of the Heart Outcomes Prevention Evaluation (HOPE) on ramipril prescribing in Ontario," Canadian Medical Association Journal, vol. 168, No. 5, pp. 553-557 (2003).

Uusitupa et al., "5-Year Incidence of Atherosclerotic Vascular Disease in Relation to General Risk Factors, Insulin Level, and Abnormalities in Lipoprotein Composition in Non-Insulin-Dependent Diabetic and Nondiabetic Subjects," Circulation, vol. 82, pp. 27-36 (1990).

Valentino et al., "A Perspective on Converting Enzyme Inhibitors and Calcium Channel Antagonists in Diabetic Renal Disease," Arch Intern Med., vol. 151, pp. 2367-2372 (1991).

Viberti et al., "Diabetec Nephropathy," Diabetes Care, vol. 15, No. 9, pp. 1216-1225 (1992).

Viberti et al., "Effect of Captopril on Progression to Clinical Proteinuria in Patients With Insulin-Dependent Diabetes Mellitus and Microalbuminaria," JAMA, vol. 26, No. 4, pp. 275-279 (1994).

Viberti, "Etiology and Prognostic Significance of Albuminuri in Diabetes," Diabetes Care, vol. 11, No. 10, pp. 840-845 (1988).

Walter et al., "Dose-response relation of the angiotensin converting enzyme inhibitor ramipril in mild to moderate essential hypertension," Am J Cardiol., vol. 59, No. 10, pp. 125D-132D (1987).

Watson et al., "Effects of captopril on glucose tolerance in elderly patients with congestive cardiac failure," vol. 12, No. 6, pp. 374-378 (1991).

Webb et al., "Vascular angiotensin conversion in humans," Journal of Cardiovascular Pharmacology, vol. 8 (suppl. 10), pp. S40-S44 (1986).

Weidmann et al., "Antihypertensive therapy in diabetic patients," Journal of Human Hypertension, vol. 6 (suppl. 2), pp. S23-S36 (1992).

Yusuf et al., "Anti-ischaemic effects of ACE inhibitors: review of current clinical evidence and ongoing clinical trials," Eur. Heart J., vol. 19 (suppl. J), pp. J36-J44 (1998).

Yusuf et al., "Beta Blockade During and After Myocardial Infarction: An Overview of the Randomized Trials," Progress in Cardiovascular Diseases, vol. XXVII, No. 5, pp. 335-371 (1985).

Yusuf et al., "Changes in Hypertension Treatment and in Congestive Heart Failure Mortality in the United States," Hypertension, vol. 13, No. 5, pp. I74-I79 (1989).

Yusuf et al., "Effect of Angiotensin-Converting Enzyme Inhibitors in Left Ventricular Dysfunction: Results of the Studies of Left Ventricular Dysfunction in the Context of Other Similar Trials," Journal of Cardiovascular Pharmacology, vol. 22 (suppl. 9), pp. S28-S35 (1993).

Yusuf et al., "Effect of enalapril on myocardial infarction and unstable angina in patients with low ejection fractions," The Lancet, vol. 340, No. 8829, pp. 1173-1178 (1992).

Yusuf et al., "Primary and secondary prevention of myocardial infarction and strokes: an update of randomly allocated, controlled trials," Journal of Hypertension, vol. 11 (suppl. 4), pp. S61-S73 (1993).

Yusuf et al., "Randomised trial of intravenous atenolol among 16 027 cases of suspected acute myocardial infarction: ISIS-1," The Lancet, pp. 57-66 (1986).

Yusuf et al., "Randomised trial of intravenous streptokinase, oral aspirin, both, or neither among 17 187 cases of suspected acute myocardial infarction: ISIS-2," The Lancet, pp. 349-360 (1988).

Yusuf et al., "Treatment of acute myocardial infarction," Eur. Heart J., vol. 17 (suppl. F), pp. 16-29 (1996).

Yusuf, "Overview of the Design and Key Results of the Studies of Left Ventricular Dysfunction (SOLVD)," Heart Failure, vol. 9, pp. 28-40 (1993).

Zabludowski et al., "A multi-centre comparative study between ramipril and enalapril in patients with mild to moderate essential hypertension," Curr Med Res Opin., vol. 11, No. 2, pp. 93-106 (1988).

Affidavit of Dr. Abram Charles Rabinowitz dated Aug. 2, 2006 (*Sanofi-Aventis Canada Inc. and Sanofi-Aventis Deutschland GmbH vs. Novopharm Limited and The Minister of Health*, Court File No. T-1979-05).

Wiek H. van Gilst et al., "Which Patient Benefits From Early Angiotensin-Converting Enzyme Inhibition After Myocardial Infarction?; Results of One-Year Serial Echocardiographic Follow-Up From the Captopril and Thrombolysis Study (CATS)," Journal of the American College of Cardiology 28(1):114-121 (1996).

Compendium of Pharmaceuticals and Specialties 59-61 (2000 35th Edition).

McMaster University Press Release of May 11, 1999, entitled *Preliminary findings of a Hamilton-led international study will revolutionize blood pressure lowering treatments with heart disease.*

"Drug reduces heart, stroke deaths in study," The Record at A3 (May 11, 1999).

"Ramipril a breakthrough in heart care?" The Gazette (May 11, 1999).

"Heart drug hailed to save millions of lives—Finding from major international study called one of biggest ever in cardiology," The Edmonton Journal at A11 (May 11, 1999).

"Researchers call off $11-million heart study," The Record (Kitchener) at A3 (May 10, 1999).

"$11 million heart study called off," The Calgary Herald at A7 (May 9, 1999).

"Study ended into vitamin E effect on heart," The Edmonton Journal at A7 (May 9, 1999).

"Heart study scraped," The Ottawa Sunday Sun at 15 (May 9, 1999).

"Vitamin-E heart study halted," The Ottawa Citizen at A6 (May 9, 1999).

P.U. Witte et . al., "Pharmacokinetics and Pharmacodynamics of a Novel Orally Active Angtiotensin Converting Enzyme Inhibitor (HOE 498) in Healthy Subjects," European Journal of Clinical Pharmacology 27(5):577-81 (1984).

P.J. O. Manhem et al., "A dose-response study Of HOE 498, a new non-sulphydyl converting enzyme inhibitor, on blood pressure, pulse rate and the renin-angiotensin-aldosterone system in normal man," British Journal of Clinical Pharmacology 20(1):27-35 (1985).

Stephen G. Ball et al., "Clinical Pharmacology of Ramipril," American Journal of Cardiology 59:23D-27D (1987).

Peter A. Todd et al., "Ramipril-A Review of its Pharmacological Properties and Therapeutic Efficacy in Cardiovascular Disorders," Drugs 39(1):110-135 (1990).

M. Marre et al., "Small Doses of Ramipril to Reduce Microalbuminuria in Diabetic Patients with Incipient Nephropathy Independently of Blood Pressure Changes," J. Cardiovasc. Pharmacol. 18(Suppl. 2):S165-S168 (1991).

Giuseppe Paolisso et al., "ACE inhibition improves insulin-sensitivity in aged insulin resistant hypertensive patients," J. Hum. Hypertens. 6(3):175-9 (1992).

Multicentre European Research Trial With Cilazapril After Angioplasty To Prevent Transluminal Coronary Obstruction And Restenosis (MERCATOR) Study Group, "Does the New Angiotensin Converting Enzyme Inhibitor Cilazapril Prevent Restenosis After Percutaneous Transluminal Coronary Angioplasty? Results of the MERCATOR Study: A Multicenter, Randomized, Double-Blind Placebo-Controlled Trial," Circulation 86(1):100-10 (1992).

Shrikant I. Bangdiwala et al., "Studies of Left Ventricular Dysfunction (SOLVD) Registry: Rationale, Design, Methods, and Description of Baseline Characteristics," American Journal of Cardiology 70:347-53 (1992).

Thomas Unger et al., "Effect of Early Onset Angiostensin Converting October Enzyme Inhibition on Myocardial Capillaries," Hypertension 20(4):478-482 (1992).

Thomas Unger et al., "Inhibition De L'Enzyme De Conversion Et Cardioprotection: Rôle Des Bradykinines," Diabete & Métabolisme 18(2):161-169 (1992).

Wolfgang Linz et al., "Ramipril prevents left ventricular hypertrophy with myocardial fibrosis without blood pressure reduction: a one year study in rats," British Journal of Clinical Pharmacology 107(4):970-975 (1992).

Oral Presentation At the 66th Scientific Sessions Of The American Heart Association, GISSI Collaboartive Group Nov. 1993.

ISIS Collaborative Group, "ISIS-4: Randomized Study of Oral Captopril in over 50,000 Patients with Suspected Acute Myocardial Infarction," Circulation 88(4):2113 Abstract (1993).

S.G. Ball et al., "ACE inhibition, atherosclerosis and myocardial infraction-The AIRE Study in practice," European Heart Journal 15(Supplement B):20-25 (1994).

Simcha Meisel et al., "Clinical Pharmacokinetics of Ramipril," Clin. Pharmacokinet. 26(1):7-15 (1994).

Ettore Ambrosini et al., "The Effect Of The Angiotensin-Converting-Enzyme Inhibitor Zofenopril On Mortality And Morbidity After Anterior Myocardial Infarction," New England Journal of Medicine 332(1):80-5 (1995).

Michel Lièvre et al., "Ramipril-Induced Regression of Left Ventricular Hypertrophy in Treated Hypertensive Individuals," Hypertension 25(1):92-7 (1995).

Torstein Gundersen et al., "Effects of 12 Weeks of Ramipril Treatment on the Quality Of Life in Patients with Moderate Congestive Heart Failure: Results of a Placebo-Controlled Trial," Cardiovascular Drugs and Therapy 9:589-594 (1995).

Marc A. Pfeffer et al., "When a Question Has an Answer: Rationale for Our Early Termination of the HEART Trial," American Journal of Cardiology 75:1173-5 (1995).

Roberto Trevisan et al., "Effect of Low-Dose Ramipril on Microalbuminuria in Normotensive or Mild Hypertensive Non-Insulin-Dependent Patients," Am. J. Hypertens. 8(9):876-83 (1995).

Enrico Agabiti-Rosei et al., "ACE inhibitor ramipril is more effective than the β-blocker atenolol in reducing left ventricular mass in hypertension. Results of the RACE (ramipril cardioprotective evaluation) study," Journal of Hypertension 13(11):1325-34 (1995).

W. Linz et al., "Experimental evidence for effects of ramipril on cardiac and vascular hypertrophy beyond blood pressure reduction," Journal D'Expression De La Société Française De Cariologie 88(2):31-34 (1995).

James E Frampton et al., "Ramipril. An Updated Review of its Therapeutic Use in Essential Hypertension and Heart Failure," Drugs 49(3):440-466 (1995).

SG Ball et al., "How ACE inhibitors reduce death from myocardial infarction: hypotheses from the AIRE Study," British Journal of Clinical Practice Supplement 84:31-35 (1996).

Ch. Schnack et al., "Renal and metabolic effects of 1-year treatment with ramipril or atenolol in NIDDM patients with microalbuminuria," Diabetologia. 39:1611-6 (1996).

Norman Kaplan, "The CARE Study: A Postmarketing Evaluation of Ramipril in 11,100 Patients," Clinical Therapeutics 18(4):658-670 (1996).

J. G. F. Cleland et al., "Effect of ramipril on morbidity and mode of death among survivors of acute myocardial infarction with clinical evidence of heart failure-A report from the AIRE Study Investigators," European Heart Journal 18:41-51 (1997).

J.A. Rodriguez et al., "A Double Blind Randomized Placebo Study Controlled Study of Ramipril vs. Sprionolacone on Left Ventricular Remolding After Acute Myocardial Infarction" Abstract 947-9, American College of Cardiology Session Mar. 16-19, 1997, Anaheim CA.

The EUCLID study group, "Randomized placebo-controlled trial of lisinopril in normotensive patients with insulin-dependent diabetes and normoalbuminuria or microalbuminuria," Lancet 349:1787-92 (1997).

Ioannis Giatras et al., "Effect of Angiotensin-Converting Enzyme Inhibitors on the Progression of Nondiabetic Renal Disease: A Meta-Analysis af Randomized Trials," Annals Of Internal Medicine 127(5):337-345 (1997).

Marc A. Pfeffer et al., "Early Versus Delayed Angiotensin-Converting Enzyme Inhibition Therapy In Acute Myocardial Infarction-The Healing and Early Afterload Reducing Therapy Trial," Circulation 95(12):2643-51 (1997).

Giulio Zuanetti et al., "Effect of the ACE Inhibitor Lisinopril on Mortality in Diabetic Patients With Acute Myocardial Infarction: Data From The GISSI-3 Study," Circulation 96(12):4239-45 (1997).

Lars Kjøller-Hansen et al., "The Angiotensin Converting Enzyme Inhibition Post Revascularization Study (APRES)" Scan. Cardiovasc. J. 32(4):225-32 (1998).

Fleming S. Nielsen et al,, "Beneficial Impact of Ramipril on Left Ventrical Hypertrophy in Normotensive Nonalbuminuria NIDDM Patients," Diabetes Care 21(5):804-809 (1998).

ACE Inhibitor Myocardial Infarction Collaborative Group, "Indications for ACE Inhibitors in the Early Treatment of Acute Myocardial Infarction: Systemic Overview of Individual Data From 100,000 Patients in Randomized Trials," Circulation 97:2202-2212 (1998).

Mordchai Ravid et al., "Use of Enalapril To Attenuate Decline in Renal Function in Normotensive, Normoalbuminuric Patients with Type 2 Diabetes," Annals of Internal Medicine 128(12 Pt. 1):982-88 (1998).

Robert E. Foster et al., "Changes in left ventricular mass and volumes in patients receiving angiotensin-converting enzyme inhibitor therapy for left ventricular dysfunction after Q-wave myocardial infarction," American Heart Journal 136(2):269-75 (1998).

Somboon Vongterapak et al., "Impediment of the Progressions of Microalbuminuria and Hyperlipidemia in Normotensive Type 2 Diabetes by Low-Dose Ramipril," Journal Of The Medical Association Of Thailand 81(9):671-81 (1998).

Tan Nguyen et al., "Postinfarction Survival and Inducibility of Ventricular Arrhythmias in the Spontaneously Hypertensive Rat-Effects of Ramipril and Hydralazine," Circulation 98:2074-2080 (1998).

Ole Kongstad-Rasmussen et al., "Treatment with Ramipril Improves Systolic Function Even in Patients with Mild Systolic Dysfunction and Symptoms of Heart Failure after Acute Myocardial Infarction," Clinical Cardiology 21:807-811 (1998).

Peter K. Schädlich et al., "Cost Effectiveness Analysis of Ramipril in Heart Failure after Myocardial Infarction-Economic Evaluation of the Acute Infarction Ramipril Efficacy December (AIRE) Study for Germany from the Perspective of Statutory Health Insurance," Pharmacoeconomics 14(6):653-669 (1998).

Rayaz A Malik et al., "Effect of angiotensin-converting enzyme (ACE) inhibitor trandolapril on human diabetic neuropathy: randomised double-blind controlled trial," The Lancet 352:1978-1981 (1998).

Federico Cacciapuoti et al., "Prevention of left ventricular hypertrophy by ACE-inhibitor, ramipril in comparison with calcium channel antagonist, felodipine," International Journal of Cardiology 63:175-178 (1998).

R. Fogari et al., "Long-term effects of ramipril and nitrendipine on albuminuria in hypertensive patients with type II diabetes and impaired renal function," Journal of Human Hypertension 13:47-54 (1999).

Konstantinos S. Sparagias et al., "Ramipril Reduces QT dispersion in Patients With Acute Myocardial Infarction and Heart Failure," American Journal of Cardiology 83:969-971 (1999).

Elisabeth R. Mathiesen et al., "Randomized controlled trial of long term efficacy of captopril on preservation of kidney function in normotensive patients with insulin dependent diabetes and microalbuminuria," BMJ 319:24-25 (1999).

Salim Yusef et al., "Summary Of Randomized Trials Of ACE Inhibitors" Clinical and Experimental Hypertension 21(5&6):835-45 (1999).

Geoffrey R. Sheinfeld et al., "Benefits of Combination Angiotensin-Converting Enzyme Inhibitor and Calcium Antagonist Therapy for Diabetic Patients," American Journal of Hypertension 12:80S-85S (1999).

CMAJ 168(13):1647-48 (2003) [see L. Pilote, "Ramipril use in Canada: HOPE or HYPE," JAMC 168(5):568-69 (2003)].

K.S. Spargias et al., "βBlocker treatment and other prognostic variables in patients with clinical evidence of heart failure after acute myocardial infarction: evidence from the AIRE study," Heart 81:25-32 (1999).

R. Willenheimer et al., "$AT_1$—receptor blockers in hypertension and heart failure: clinical experience and future directions," European Heart Journal 20:997-1008 (1999).

F. Šimko et al., "Heart Failure and Angiotensin Converting Enzyme Inhibition: Problems and Perspectives," Physiological Research 48:1-8 (1999).

GISSI-3 Investigators et al., "Aspirin does not Affect Circulatory or Renal Effects of Lisinopril early after Myocardial Infarction," Circulation 88(4):2998 Abstract (1993).

H.U. Janka et al., "Metabolic Effects on Ramlpril Treatment in Hypertensive Subjects with Non-Insulin-Dependent Diabetes Mellitus," Arzneimittel-Forschung, 1990, vol. 40, No. 4, pp. 432-435.

Gerstein et al., "Effects of ramipril on cardiovascular and microvascular outcomes in people with diabetes mellitus: results of the HOPE study and MICRO-HOPE substudy," The Lancet, 2000, vol. 355, pp. 253-259.

J. Krützfeldt et al., "Ramipril increases the protein level of skeletal muscle IRS-1 and alters protein tyrosine phosphatase activity in spontaneously hypertensive rats," Naunyn-Schmiedeberg's Archives of Pharmacology, 2000, vol. 362, No. 1, pp. 1-6.

Ferruccio Galletti et al., "Controlled study of the effect of angiotensin converting enzyme inhibition versus calcium-entry blockade on insulin sensitivity in overweight hypertensive patients: Trandolapril Italian Study (TRIS)," Journal of Hypertension, Current Science, 1999, vol. 17, No. 3, pp. 439-445.

Taha Keilani, MD et al., "Selected Aspects of ACE Inhibitor Therapy for Patients with Renal Disease: Impact on Proteinuria, Lipids and Potassium," Journal of Clinical Pharmacology, 1995, vol. 35, No. 1, pp. 87-97.

George L. Bakris et al., "ACE inhibition or angiotensin receptor blockade: Impact on potassium in renal failure," Kidney International, 2000, vol. 58, No. 5, pp. 2084-2092.

P. O. Carlsson et al., "Angiotensin II and the endocrine pancreas: effects on islet blood flow and insulin secretion in rats," Diabetologia, 1998, vol. 41, No. 2, pp. 127-133.

M. Tahmasebi et al., "The tissue renin-angiotensin system in human pancreas," Journal of Endocrinology, 1999, vol. 161, No. 2, pp. 317-322.

Salim Yusef et al., "Ramipril and the Development of Diabetes," JAMA, 2001, vol. 286, No. 15, pp. 1882-1885.

Kathleen M. Gillespie, "Type I diabetes: Pathogenesis and Prevention," Review CMAJ, pp. 165-170 (Jul. 18, 2006).

Interview Summary dated May 10, 2006, in U.S. Appl. No. 09/645,556.

Office Action dated Nov. 2, 2001, in U.S. Appl. No. 09/651,275.

Office Action dated Mar. 14, 2002, in U.S. Appl. No. 09/651,275.

Office Action dated Oct. 1, 2002, in U.S. Appl. No. 09/651,275.

Office Action dated Jun. 1, 2004, in U.S. Appl. No. 10/694,001.

Office Action dated May 3, 2004, in U.S. Appl. No. 10/694,001.

Office Action dated Jul. 29, 2004, in U.S. Appl. No. 10/694,001.

Office Action dated Apr. 19, 2005, in U.S. Appl. No. 10/694,001.

Notice of Allowance dated Oct. 31, 2005, in U.S. Appl. No. 10/694,001.

Notice of Allowance dated Apr. 24, 2006, in U.S. Appl. No. 10/694,001.

Office Action dated Sep. 21, 2007, in U.S. Appl. No. 11/001,028.

Office Action dated Jun. 7, 2007, in U.S. Appl. No. 10/492,919.

Office Action dated Aug. 22, 2007, in U.S. Appl. No. 10/492,919.

International Search Report mailed Sep. 17, 2001, of International Application No. PCT/EP00/08341.

International Search Report mailed Jun. 18, 2001, of International Application No. PCT/EP00/08461.

International Search Report mailed Oct. 16, 2003, of International Application No. PCT/EP02/11636.

Summons to attend oral proceedings pursuant to Rule 71(1) EPC dated Oct. 18, 2007.

Summons to attend oral proceedings pursuant to Rule 71(1) EPC dated Nov. 23, 2007 for Application No. 00965906.1 (EP 1 216 038).

Office Action dated Nov. 23, 2007 in U.S. Appl. No. 11/001,028.

USE OF INHIBITORS OF THE RENIN-ANGIOTENSIN SYSTEM IN THE PREVENTION OF CARDIOVASCULAR EVENTS

This application is a continuation of application Ser. No. 10/694,001, filed on Oct. 28, 2003, now abandoned which is a continuation of application Ser. No. 09/651,275, filed on Aug. 30, 2000, now abandoned which claims the benefit of priority to U.S. provisional Application No. 60/151,436, filed on Aug. 30, 1999, all of which are incorporated herein by reference.

FIELD OF THE INVENTION

The present invention relates to the use of an inhibitor of the renin-angiotensin system or a pharmaceutically acceptable derivative thereof, optionally together with another antihypertensive, a cholesterol lowering agent, a diuretic or aspirin, in the manufacture of a medicament for the prevention of cardiovascular events; to a method of preventing cardiovascular events comprising administering to a patient in need of such prevention an effective amount of an inhibitor of the renin angiotensin system or a pharmaceutically acceptable derivative thereof, optionally together with another antihypertensive, a cholesterol lowering agent, a diuretic or aspirin; or to a combination product containing an inhibitor of the renin-angiotensin system or a pharmaceutically acceptable derivative thereof and a cholesterol lowering agent.

BACKGROUND OF THE INVENTION

The renin-angiotensin system (RAS) can be interfered with by inhibition of the enzymes synthesizing angiotensins or by blocking the corresponding receptors at the effector sites. There are many marketed or investigation-stage agents which inhibit RAS activity, and many fall into two broad classes: the inhibitors of angiotensin-converting enzyme (ACE), whose approved names generally end in "-pril" or in the case of active metabolites "-prilat", and antagonists at angiotensin receptors (more specifically, currently, the $AT_1$ receptor) (Angiotensin II Antagonists), whose approved names generally end in "-sartan". Also potentially of increasing importance may be a class of drugs known as neutral endopeptidase (NEP) inhibitors which will also have an ACE-inhibitory effect or the potential to reduce RAS activity and are therefore also known as NEP/ACE-inhibitors.

ACE inhibitors are well known in the art for their activity in inhibiting angiotensin converting enzyme, thereby blocking conversion of the decapeptide angiotensin I to angiotensin II. The principal pharmacological and clinical effects of ACE inhibitors arise from suppression of synthesis of angiotensin II. Angiotensin II is a potent pressor substance and, therefore, blood pressure lowering can result from inhibition of its biosynthesis, especially in animals and humans whose hypertension is angiotensin II related. ACE inhibitors are effective antihypertensive agents in a variety of animal models and are clinically useful for the treatment of hypertension in humans.

ACE inhibitors are also employed for the treatment of heart conditions such as hypertension and heart failure. It is known that at least some ACE inhibitors can improve (i.e., decrease) morbidity and mortality in patient populations with heart conditions, ie. patients with low ejection fraction (EF) or heart failure (HF), but their role in a broader population of high risk patients without ventricular dysfunction or HF is unknown.

SUMMARY OF THE INVENTION

The present invention generally relates to the use of an inhibitor of the renin-angiotensin system or a pharmaceutically acceptable derivative thereof in the manufacture of a medicament for the prevention of cardiovascular events.

The present invention further relates to the use of an inhibitor of the renin-angiotensin system or a pharmaceutically acceptable derivative thereof in the manufacture of a medicament for the prevention of myocardial infarction (MI), worsening of angina, and cardiac arrest.

Furthermore, the present invention relates to the use of an inhibitor of the renin-angiotensin system or a pharmaceutically acceptable derivative thereof in the manufacture of a medicament for the prevention of cardiovascular events such as, for example, myocardial infarction (MI), worsening of angina or cardiac arrest in a patient with an increased cardiovascular risk, for example, due to a manifest coronary heart disease, a history of transient ischaemic attacks or stroke, or a history of peripheral vascular disease.

More generally, the present invention relates to the use of an inhibitor of the renin-angiotensin system or a pharmaceutically acceptable derivative thereof in the manufacture of a medicament for the prevention of cardiovascular events in patients with no evidence of left ventricular dysfunction or heart failure.

The present invention further relates to the use of an inhibitor of the renin-angiotensin system or a pharmaceutically acceptable derivative thereof in the manufacture of a medicament for the prevention of myocardial infarction (MI), stroke, cardiovascular death or overt nephropathy in a diabetic patient.

Another embodiment of the present invention is the use of an inhibitor of the renin-angiotensin system or a pharmaceutically acceptable derivative thereof together with another antihypertensive, a cholesterol lowering agent, a diuretic or aspirin in the manufacture of a medicament for the prevention of cardiovascular events, for example stroke, congestive heart failure, cardiovascular death, myocardial infarction, worsening of angina, cardiac arrest, or revascularization procedures.

Yet another embodiment of the present invention is the use of an inhibitor of the renin-angiotensin system or a pharmaceutically acceptable derivative thereof together with another antihypertensive, a cholesterol lowering agent, a diuretic or aspirin in the manufacture of a medicament for the prevention of diabetes or diabetic complications.

A further embodiment of the present invention is the use of an inhibitor of the renin-angiotensin system or a pharmaceutically acceptable derivative thereof together with another antihypertensive, a cholesterol lowering agent, a diuretic or aspirin in the manufacture of a medicament for the prevention of congestive heart failure (CHF) in a patient not previously having congestive heart failure.

Another embodiment of the present invention is a combination product containing an inhibitor of the renin-angiotensin system or a pharmaceutically acceptable derivative thereof and another antihypertensive, a cholesterol lowering agent, a diuretic or aspirin for the use in the prevention of cardiovascular events.

Yet another embodiment of the present invention is a combination product containing an inhibitor of the renin-angiotensin system or a pharmaceutically acceptable derivative thereof and a cholesterol lowering agent.

A further embodiment of the present invention is a method of preventing cardiovascular events, for example myocardial infarction, worsening of angina, and cardiac arrest, comprising administering to a patient in need of such prevention an effective amount of an inhibitor of the renin-angiotensin system or a pharmaceutically acceptable derivative thereof, particularly in patients having an increased cardiovascular risk.

Another embodiment of the present invention is a method of preventing myocardial infarction, stroke, cardiovascular death or overt nephropathy in a diabetic patient, comprising administering to said patient an effective amount of an inhibitor of the renin-angiotensin system or a pharmaceutically acceptable derivative thereof.

A further embodiment of the present invention is a method of preventing cardiovascular events, for example stroke, congestive heart failure, cardiovascular death, myocardial infarction, worsening of angina, cardiac arrest, or revascularization procedures, or diabetes or diabetic complications, comprising administering to a patient in need of such prevention an effective amount of an inhibitor of the renin-angiotensin system or a pharmaceutically acceptable derivative thereof together with an effective amount of another antihypertensive, a cholesterol lowering agent, a diuretic or aspirin (combination therapy).

Yet another embodiment of the present invention is a method of preventing congestive heart failure in a patient not previously having congestive heart failure, comprising administering to said patient an effective amount of an inhibitor of the renin-angiotensin system or a pharmaceutically acceptable derivative thereof together with an effective amount of another antihypertensive, a cholesterol lowering agent, a diuretic or aspirin (combination therapy).

DETAILED DESCRIPTION OF THE INVENTION

It has been surprisingly found that cardiovascular events such as stroke, congestive heart failure, cardiovascular death, myocardial infarction, worsening of angina, cardiac arrest, or revascularization procedures such as coronary artery bypass graft surgery (CABG), PTCA, Peripheral Angioplasty Surgery, Amputation, Carotid Endarterectomy and metabolic disorders such as diabetes or diabetic complications such as overt nephropathy, renal dialysis or laser therapy, or new microalbuminuria can be prevented in a broad population of high risk patients with no evidence of left ventricular dysfunction or heart failure, by use of an inhibitor of the RAS system.

Furthermore and very surprisingly, the prevention of such cardiovascular events is also observed in a very broad range of high risk patients in addition to other effective therapies with, for example, antihypertensives (other than inhibitors of the RAS system), diuretics, cholesterol lowering agents or aspirin.

Thus the present invention describes a new method to prevent cardiovascular events, comprising administering to a patient in need of such prevention an effective amount of an inhibitor of the renin angiotensin system or a pharmaceutically acceptable derivative thereof, optionally together with another antihypertensive, a cholesterol lowering agent, a diuretic or aspirin.

High risk patients are, for instance, those patients which are at risk of having a cardiovascular event due to a manifest coronary heart disease, a history of transient ischaemic attacks or stroke, or a history of peripheral vascular disease. Another group of high risk patients include those patients with diabetes.

The phrase "diabetes" as used herein includes both type I diabetes, also known as insulin-dependent, diabetes mellitus (IDMM), and type II diabetes, also known as non-insulin-dependent diabetes mellitus (NIDDM).

The phrase "diabetic complications" as used herein includes overt nephropathy, need for laser therapy or dialysis.

The phrase "inhibitor of the renin-angiotensin system (RAS) or a pharmaceutically accetable derivative thereof" as used herein includes any compound which by itself or upon administration blocks the negative effects of angiotensin II on the vasculature either by reducing the synthesis of angiotensin II or blocking its effect at the receptor.

Inhibitors of the RAS include ACE inhibitors, Angiotensin II antagonists and renin inhibitors and pharmaceutically acceptable derivatives thereof including prodrugs and metabolites.

The phrase "angiotensin converting enzyme inhibitor" ("ACE inhibitor") is intended to embrace an agent or compound, or a combination of two or more agents or compounds, having the ability to block, partially or completely, the rapid enzymatic conversion of the physiologically inactive decapeptide form of angiotensin ("Angiotensin I") to the vasoconstrictive octapeptide form of angiotensin ("Angiotensin II"). The phrase "ACE inhibitor" also embraces so-called NEP/ACE inhibitors (also referred to as selective or dual acting neutral endopeptidase inhibitors) which possess neutral endopeptidase (NEP) inhibitory activity and angiotensin converting enzyme (ACE) inhibitory activity.

Examples of ACE inhibitors suitable for use herein are, for instance, the following compounds: AB-103, ancovenin, benazeprilat, BRL-36378, BW-A575C, CGS-13928C, CL242817, CV-5975, Equaten, EU-4865, EU-4867, EU-5476, foroxymithine, FPL 66564, FR-900456, Hoe-065, I5B2, indolapril, ketomethylureas, KRI-1177, KRI-1230, L681176, libenzapril, MCD, MDL-27088, MDL-27467A, moveltipril, MS-41, nicotianamine, pentopril, phenacein, pivopril, rentiapril, RG-5975, RG-6134, RG-6207, RGH0399, ROO-911, RS-10085-197, RS-2039, RS 5139, RS 86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y-23785, Yissum, P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, 1(-(I-carboxy-6-(4-piperidinyl)hexyl)amino)-1-oxopropyl octahydro-IH-indole-2-carboxylic acid, Bioproject BP1.137, Chiesi CHF 1514, Fisons FPL-66564, idrapril, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril.

A group of ACE inhibitors of high interest are alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril.

Many of these ACE inhibitors are commercially available, especially those listed in the above group. For example, a highly preferred ACE inhibitor ramipril (known from EP 79022) is sold by Aventis, e.g. under the trademark Delix® or Altace®. Enalapril or Enalapril Maleate, and Lisinopril are two more highly preferred ACE inhibitors sold by Merck & Co. Enalapril is sold under the trademark Vasotec®. Lisinopril is sold under the trademark Prinivil®.

Examples of NEP/ACE inhibitors suitable for use herein include those disclosed in U.S. Pat. Nos. 5,508,272, 5,362,727, 5,366,973, 5,225,401, 4,722,810, 5,223,516, 5,552,397, 4,749,688, 5,504,080, 5,612,359, 5,525,723, 5,430,145, and 5,679,671, and European Patent Applications 0481522, 0534263, 0534396, 0534492 and 0671172.

Preferred are those NEP/ACE inhibitors which are designated as preferred in the above U.S. patents and European Patent Applications and are incorporarted herein by reference. Especially preferrred is the NEP/ACE inhibitor omapatrilat (disclosed in U.S. Pat. No. 5,508,272), or MDL100240 (disclosed in U.S. Pat. No. 5,430,145).

The phrase "angiotensin II antagonist" is intended to embrace an agent or compound, or a combination of two or more agents or compounds, having the ability to block, partially or completely the binding of angiotensin II at angiotensin receptors, specifically at the $AT_1$ receptor.

Examples of Angiotensin II Antagonists suitable for use herein are, for instance, the following compounds:

Saralasin acetate, candesartan cilexetil, CGP-63170, EMD-66397, KT3-671, LR-B/081, valsartan, A-81282, BIBR-363, BIBS-222, BMS-184698, candesartan, CV-11194, EXP-3174, KW-3433, L-161177, L-162154, LR-B/057, LY-235656, PD-150304, U-96849, U-97018, UP-275-22, WAY-126227, WK-1492.2K, YM-31472, losartan potassium, E-4177, EMD-73495, eprosartan, HN-65021, irbesartan, L-159282, ME-3221, SL-91.0102, Tasosartan, Telmisartan, UP-269-6, YM-358, CGP-49870, GA-0056, L-159689, L-162234, L-162441, L-163007, PD-123177, A-81988, BMS-180560, CGP-38560A, CGP-48369, DA-2079, DE-3489, DuP-167, EXP-063, EXP-6155, EXP-6803, EXP-7711, EXP-9270, FK-739, HR-720, ICI-D6888, ICI-D7155, ICI-D8731, isoteoline, KRI-1177, L-158809, L-158978, L-159874, LR B087, LY-285434, LY-302289, LY-315995, RG-13647, RWJ-38970, RWJ-46458, S-8307, S-8308, saprisartan, saralasin, Sarmesin, WK-1360, X-6803, ZD-6888, ZD-7155, ZD-8731, BIBS39, CI-996, DMP-811, DuP-532, EXP-929, L-163017, LY-301875, XH-148, XR-510, zolasartan and PD-123319.

A group of Angiotensin II Antagonists of high interest are saralasin acetate, candesartan cilexetil, valsartan, candesartan, losartan potassium, eprosartan, irbesartan, tasosartan, or telmisartan.

Examples of renin inhibitors suitable for use herein are, for instance, the following compounds: enalkrein; RO 42-5892; A 65317; CP 80794; ES 1005; ES 8891; SQ 34017; CGP 29287; CGP 38560; SR 43845; U-71038; A 62198; A 64662, A-69729, FK 906 and FK 744.

Pharmaceutically acceptable derivatives of RAS inhibitors are understood to include physiologically tolerable salts of RAS inhibitors, such physiologically tolerable salts are understood as meaning both their organic and inorganic salts, such as are described in Remington's Pharmaceutical Sciences (17th Edition, page 1418 (1985)). On account of the physical and chemical stability and the solubility, for acidic groups, inter alia, sodium, potassium, calcium and ammonium salts are preferred; for basic groups, inter alia, salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid are preferred.

The RAS inhibitors suitable for use herein or their pharmaceutically acceptable derivatives can be used in animals, preferably in mammals, and in particular in humans, as pharmaceuticals per se, in mixtures with one another or in the form of pharmaceutical preparations.

The present invention also relates to pharmaceutical formulations comprising as active ingredient at least one RAS inhibitor and/or pharmaceutically acceptable derivative thereof in addition to customary pharmaceutically innocuous excipients and auxiliaries and their use in the prevention of cardiac events and the production of medicaments therefor. The pharmaceutical preparations normally contain 0.1 to 99 percent by weight, preferably 0.5 to 95 percent by weight, of the RAS inhibitor and/or a pharmaceutically acceptable derivative thereof. The pharmaceutical preparations can be prepared in a manner known per se. To this end, the RAS inhibitor and/or a pharmaceutically acceptable derivative thereof are brought, together with one or more solid or liquid pharmaceutical excipients and/or auxiliaries and, if desired, in combination with other pharmaceutical active compounds, into a suitable administration form or dose form, which can then be used as a pharmaceutical in human medicine or veterinary medicine.

Pharmaceuticals which contain a RAS inhibitor and/or a pharmaceutically acceptable derivative thereof can be administered orally, parenterally, intravenously, rectally or by inhalation, the preferred administration being dependent on the particular symptoms of the disorder. The RAS inhibitors and/or pharmaceutically acceptable derivatives thereof can be used here on their own or together with pharmaceutical auxiliaries, namely both in veterinary and in human medicine.

The person skilled in the art is familiar on the basis of his expert knowledge with the auxiliaries which are suitable for the desired pharmaceutical formulation. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers or colorants.

For an oral administration form, the active compounds are mixed with the additives suitable therefor, such as excipients, stabilizers or inert diluents and are brought by means of the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. Preparation can take place here both as dry and as moist granules. Possible oily excipients or solvents are, for example, vegetable or animal oils, such as sunflower oil or codliver oil.

For subcutaneous or intravenous administration, the active compounds are brought into solution, suspension or emulsion, if desired with the substances customary therefor such as solubilizers, emulsifiers or other auxiliaries. Suitable solvents, for example, are: water, physiological saline solution or alcohols, e.g. ethanol, propanol, glycerol, and additionally also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound in a pharmaceutically acceptable solvent, such as, in particular, ethanol or water, or a mixture of such solvents.

If required, the formulation can also contain other pharmaceutical auxiliaries such as surfactants, emulsifiers and stabilizers, and also a propellant. Such a preparation customarily contains the active compound in a concentration from approximately 0.1 to 10, in particular from approximately 0.3 to 3% by weight.

The dose of the active compound to be administered and the frequency of administration will depend on the potency and duration of action of the compounds used; additionally also on the nature of the indication and on the sex, age, weight and individual responsiveness of the mammal to be treated.

On average, the daily dose in a patient weighing approximately 75 kg is at least 0.001 mg/kg, preferably 0.01 mg/kg, to about 20 mg/kg, preferably 1 mg/kg, of body weight.

The RAS inhibitors and/or pharmaceutically acceptable derivatives thereof can also be used to achieve an advantageous therapeutic action together with other pharmacologically active compounds for the prevention of the abovementioned syndromes.

The present invention furthermore relates to a combination product containing an inhibitor of the renin-angiotensin system or a pharmaceutically acceptable derivative thereof and another antihypertensive, a cholesterol lowering agent, a diuretic or aspirin for the use in the prevention of cardiovascular events.

The invention additionally relates very generally to the combination of a RAS inhibitor and/or a pharmaceutically acceptable derivative thereof with a cholesterol lowering agent.

In addition to administration as a fixed combination, the invention also relates to the simultaneous, separate or sequential administration of an RAS inhibitor and/or pharmaceutically acceptable derivative thereof with another antihypertensive, a cholesterol lowering agent, a diuretic or aspirin.

The invention additionally relates to a pharmaceutical preparation comprising an RAS inhibitor and/or a pharmaceutically acceptable derivative thereof and a cholesterol lowering agent (combination product).

The pharmaceutical preparations of the combination product according to the invention can be prepared, for example, by either intensively mixing the individual components as a powder, or by dissolving the individual components in the suitable solvent such as, for example, a lower alcohol and then removing the solvent.

The weight ratio of the RAS inhibitor and/or a pharmaceutically acceptable derivative thereof and the cholesterol lowering agent in the novel combinations and preparations lies in the range from 1:0.01 to 1:100, preferably 1:0.1 to 1:10.

The novel combinations and preparations in total may contain 0.5-99.5% by weight, in particular 4-99% by weight, of these active compounds.

When used according to the invention in mammals, preferably in human, the doses of the various active compound components, for example, vary in the range from 0.001 to 100 mg/kg/day.

Typically, the individual daily dosages for these combinations can range from about one-fifth of the minimally recommended clinical dosages to the maximum recommended levels for the entities when they are given singly.

By means of combined administration, the effect of one combination component can be potentiated by the other respective component, i.e. the action and/or duration of action of a novel combination or preparation is stronger or longer lasting than the action and/or duration of action of the respective individual components (synergistic effect). This leads on combined administration to a reduction of the dose of the respective combination component, compared with individual administration. The novel combinations and preparations accordingly have the advantage that the amounts of active compound to be administered can be significantly reduced and undesired side effects can be eliminated or greatly reduced.

A preferred combination product would contain, for instance, as a RAS inhibitors alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat or spirapril, most preferably ramipril and as a cholesterol lowering agent lovastatin, pravastatin, simvastatin or fluvastatin.

The phrase "combination therapy", in defining use of an inhibitor of the RAS system together with another antihypertensive, a cholesterol lowering agent, a diuretic or aspirin is intended to embrace administration of each agent in a sequential manner in a regimen that will provide beneficial effects of the drug combination, and is intended as well to embrace co-administration of these agents in a substantially simultaneous manner, such as by oral ingestion of a single capsule having a fixed ratio of these active agents or ingestion of multiple, separate capsules for each agent.

"Combination therapy" will also include simultaneous or sequential administration by intravenous, intramuscular or other parenteral routes into the body, including direct absorption through mucous membrane tissues, as found in the sinus passages. Sequential administration also includes drug combination where the individual elements may be administered at different times and/or by different routes but which act in combination to provide a beneficial effect.

The phrase "effective amount" is intended to qualify the amount of each agent for use in the combination therapy which will achieve the goal of preventing cardiac events while avoiding adverse side effects typically associated with each agent.

Examples of classes of other antihypertensives for use in the combination product or useful in the combination therapy are for example calcium channel blockers (or calcium antagonists) and beta-blockers.

Useful beta-blockers include timolol, atenolol, metoprolol, propanolol, nadolol and pindololpropanolol.

Useful calicum channel blockers include diltiazem, felodipine, nifedipine, amlodipine, nimodipine, isradipine, nitrendipine and verapamil.

Useful diuretics include methyclothiazide, hydrochlorothiazide, torsemide, metolazone, furosemide, chlorthalidone, N-(5-sulfamoyl-1,3,4-thiadiazol-2-yl)acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid.

An example for useful cholesterol lowering agents are statins.

The conversion of 3-hydroxy-Omethylglutaryl-coenzyme A (HMGCoA) to mevalonate is an early and rate-limiting step in the cholesterol biosynthetic pathway. This step is catalyzed by the enzyme HMOCoA reductase. Statins inhibit HMGCoA reductase from catalyzing this conversion. As such, statins are collectively potent cholesterol lowering agents.

Statins include such compounds as simvastatin, disclosed in U.S. Pat. No. 4,444,784, pravastatin, disclosed in U.S. Pat. No. 4,346,227, cerivastatin, disclosed in U.S. Pat. No. 5,502,199 mevastatin, disclosed in U.S. Pat. No. 3,983,140, velostatin, disclosed in U.S. Pat. No. 4,448,784 and U.S. Pat. No. 4,450,171; fluvastatin, disclosed in U.S. Pat. No. 4,739,073, compactin, disclosed in U.S. Pat. No. 4,804,770; lovastatin, disclosed in U.S. Pat. No. 4,231,938; dalvastatin, disclosed in EP-A 738510, fluindostatin, disclosed in EP-A 363934; atorvastatin, disclosed in U.S. Pat. No. 4,681,893, atorvastatin calcium, disclosed in U.S. Pat. No. 5,273,995; and dihydrocompactin, disclosed in U.S. Pat. No. 4,450,171, all of the above mentioned documents being incorporated herein by reference.

Preferred statins include lovastatin, pravastatin, simvastatin and fluvastatin.

Aspirin irreversibly inactivates platelet cyclooxygenase by acetylating this enzyme at the active site. In addition to reducing mortality, aspirin also reduces strokes and myocardial infarction. The exact mechanisms of the benefit of aspirin is not known.

EXAMPLES

The examples as set forth herein are meant to exemplify the various aspects of carrying out the present invention and are not intended to limit the invention in any way.

A large-scale clinical trial (HOPE (Heart Outcomes Prevention Evaluation) Study) was designed to examine the effect of the ACE inhibitor ramipril versus placebo in reducing cardiovascular events. 9,297 high risk patients ($\geq$55 yrs with evidence of vascular disease or diabetes plus one additional risk factor), without known low EF or HF were randomized to receive Ramipril (2.5 mg to 10 mg/day) or matching placebo for a mean duration of 5 years. The primary outcome was the first occurrence of the composite of cardiovascular (CV) mortality, myocardial infarction or stroke. The study was stopped at 4.5 years by the independent Data and Safety Monitoring Board because of convincing evidence of benefit. 646 (13.9%) patients allocated to Ramipril and 816 (17.5%) placebo patients experienced a primary outcome (Relative risk, RR of 0.78, 95% confidence interval of 0.70-0.86; Portable=0.000002). There were clear and significant reductions separately in CV deaths (6.0% v. 8.0%, RR of 0.75, Portable=0.0002), myocardial infarction (9.8% v.12.0%, RR of 0.68, Portable=0.0002). Secondary outcomes such as total mortality (10.3% v. 12.2%, RR of 0.00035), revascularization procedures (16.0% v. 18.4%, RR of 0.85, Portable=0.0013), cardiac arrests (0.8% v. 1.2%, RR of 0.63; Portable=0.03), heart failure (7.4% v. 9.4%, RR of 0.78; Portable=0.0005), and diabetic complications (6.4% v. 7.7%, RR 0.85; Portable=0.017), were also significantly reduced. Other outcomes included worsening or new angina, or new heart failure (irrespective of hospitalization).

Ramipril significantly reduces mortality, myocardial infarction, stroke, revascularization procedures, and heart failure and prevents diabetic complications in a broad range of high risk patients without low EF or heart failure.

The protocols and results are set forth in the Examples presented hereinbelow.

Example 1

Study Design

In a double blind, 2×2 factorial, randomized trial, HOPE evaluated Ramipril or vitamin E in 9541 patients. A substudy of 244 patients tested a low dose (2.5 mg/day) versus the full dose (10 mg/day) of Ramipril. The primary outcome in these 244 patients is reported as a footnote to Table 3. Therefore the main results report is on 9,297 patients randomized to receive 10 mg Ramipril or equivalent placebo. The effects of vitamin E are reported separately. The design of HOPE has been published (Can J Cardiology 1996; 12(2); 127-137), a brief summary follows below:

Patient Inclusion/Exclusion

Men and women were eligible if aged 55 years and older, with prior coronary artery disease, stroke, peripheral vascular disease or diabetes plus at least one other risk factor (current or previous hypertension, elevated total cholesterol, low HDL cholesterol, current cigarette smoking, known microalbuminuria or previous vascular disease). Patents who had HF, were known to have low EF, those on ACE-I or vitamin E, those with uncontrolled hypertension or overt nephropathy, or recent MI (<4 weeks) were excluded. In this large, simple trial it was impractical to measure left ventricular function in all patients (none of whom had heart failure or were considered to need an ACE-I). Instead, echocardiograms were done in all patients (n=496) from 3 centres who entered a substudy. 2.6% were found to have an EF<0.40. Additionally, an audit of charts identified that in 5285 patients a prerandomization and evaluation of ventricular function had been conducted. Only 409 (7.7%) were documented to have low EF and none had heart failure prior to randomization. A separate analysis of those documented to have a preserved EF (n=4876) is provided. After obtaining written informed consent, all eligible patients entered a run in phase where they received 2.5 mg Ramipril OD for 7-10 days followed by matching placebo for 10-14 days. Patients who were non compliant (<80% of pills taken), who experienced side effects, developed abnormal creatinine or potassium levels or those who withdrew consent were excluded. 9,541 were included; 9,297 were randomized to receive Ramipril at 10 mg/day or matching placebo, with 244 randomized to low dose (2.5 mg/day) of Ramipril.

At randomization, patients were allocated to receive Ramipril at 2.5 mg OD for one week, then 5 mg OD for another 3 weeks, followed by 10 mg once daily, or matching placebo. Additionally, all patients were randomized to vitamin E 400 IU/day or matching placebo. Follow-up visits occurred at 1 month, 6 months and then at 6 month intervals. At each visit, data were collected on events, compliance, and side effects leading to alteration of study medications. All primary and secondary events were documented on additional forms and were centrally adjudicated using standardized definitions.

Study organization: Patients were recruited over an 18 month period (December 1993 to June 1995) from centres in Canada (129), the USA (27), 14 Western European countries (76), Argentina and Brazil (30), and Mexico (5). Each institution's review board approved the protocol. The study was organized and coordinated by the Canadian Cardiovascular Collaboration Project Office located at the Preventive Cardiology and Therapeutics Research Program, Hamilton Health Sciences Corporation Research Centre, McMaster University, Hamilton, Canada. Adjunct project offices were located in London, England; São Paulo, Brazil and Rosario, Argentina. The responsibility for the overall study was undertaken by the Steering Committee.

Statistical Analyses: The study was originally designed to follow participants for a mean of 3.5 years. However, before the end of this period, the Steering Committee (blinded to any results) postulated a possible lag before treatment would have its full effects and recommended extension of follow up to 5 years. Assuming an event rate of 4% per year for 5 years, with 9,000 patients there would be 90% power to detect a 13.5% relative risk reduction utilizing a 2 sided alpha of 0.05, analyzed on an intention to treat basis. Survival curves were estimated using the Kaplan-Meier procedure and compared treatments utilizing a log-rank test. Because of the factorial design, all analyses were stratified for the randomization to vitamin E or control. Subground analyses were conducted utilizing tests for interaction in the Cox regression model. This model was also used for treatment effect estimates adjusted for any imbalances in key prognostic factors. The adjusted and unadjusted analyses provided virtually identical results, so only the unadjusted estimates are provided.

Interim analysis, data monitoring and early termination: An independent Data and Safety Monitoring Board (DSMB) monitored the progress of all aspects of the study. Four formal interim analyses were planned. The statistical monitoring boundary for benefit required crossing four standard deviations for the first half of the trial and three standard deviations in the second half. For harm the respective boundaries were three and two standard deviations respectively. The decision to stop or continue the trial would depend on a number of additional factors including consistency of results across key subgroups. On Mar. 22, 1999, the independent DSMB recommended termination of the trial because of clear and persistent evidence of benefit of Ramipril which had consistently and clearly crossed the monitoring boundaries on two consecutive looks. (20% relative risk reduction in the primary outcome with 95% Cl of 12% to 28%, Z of −4.5; p=0.00001). The results of the trial were disclosed to the investigators at two meetings held on April 17$^{th}$ and April 24$^{th}$. A cut off for all events for the main analysis was set for Apr. 15, 1999. Close our visits commenced on April 19$^{th}$ and were scheduled to be completed by Jun. 30, 1999.

Example 2

Patient Characteristics:

Table 1 provides the baseline characteristics of patients entering the trial. Of note there were 2480 women (26.7%), 5128 individuals≧65 years (55.2%), 8160 with vascular disease (87.8%), 4355 with a history of hypertension (46.8%) and 3578 with diabetes (38.5%). This makes HOPE the largest trial of ACE-I in women, the elderly and among diabetics and with a sizeable number of high risk hypertensives.

TABLE 1

Baseline Characteristics of the HOPE Study Patients

| | Ramipril n (%) | Placebo N (%) |
|---|---|---|
| No. Randomized | N = 4645 | N = 4652 |
| Mean Age | 66 (7) | 66 (7) |
| No. Women | 27.5 | 25.8 |
| History of Coronary artery disease | 3691 (79.5) | 3784 (81.3) |
| Myocardial infarction | 2410 (51.9) | 2482 (53.4) |
| ≦1 year | 452 (9.7) | 445 (9.6) |
| >1 year | 1985 (42.7) | 2070 (44.5) |
| Stable angina pectoris | 2538 (54.6) | 2609 (56.1) |
| Unstable angina pectoris | 1179 (25.4) | 1188 (25.5) |
| CABG surgery | 1192 (25.7) | 1207 (25.9) |
| PTCA | 853 (18.4) | 806 (17.3) |
| Stroke or Transient ischemic attacks | 500 (10.8) | 513 (11.0) |
| Peripheral Vascular disease | 1963 (42.3) | 2083 (44.8) |
| Hypertension | 2212 (47.6) | 2143 (46.1) |
| Diabetes | 1808 (38.9) | 1770 (38.0) |
| Known elevated total cholesterol | 3036 (65.4) | 3089 (66.4) |
| Known low LDL | 842 (18.1) | 882 (19.0) |
| Current cigarette smoking | 645 (13.9) | 674 (14.5) |
| Drugs at Baseline: | | |
| Beta Blockers | 1820 (39.2) | 1853 (39.8) |
| Aspirin/other antiplatelets | 3497 (75.3) | 3577 (76.9) |
| Lipid lowering agent | 1318 (28.4) | 1340 (28.8) |
| Diuretics | 713 (15.3) | 706 (15.2) |
| Calcium channel blockers | 2152 (46.3) | 2228 (47.9) |
| ECG left ventricular hypertrophy | 378 (8.1) | 405 (8.7) |
| No. With microalbuminuria | 955 (20.6) | 1008 (21.7) |
| Blood Pressure | 139/79 | 139/79 |
| Heart Rate | 69 | 69 |
| Body Mass Index | 28 | 28 |

CABG = Coronary artery bypass graft surgery,
PTCA = Percutaneous transhuminal coronary angioplasty,
No. = number,
LDL = Low density Lipoprotein. Peripheral vascular disease includes claudication, history of peripheral arterial disease or ankle-arm BP ratio of <0.90.

Example 3

Compliance

Among those allocated to the Ramipril group, the proportion taking study or open label ACE-I was 87.4% at 1 year, 85.2% at 2 years, 82.2% at 3 years, 75.5% at 4 years and 78.3% at the final visit. 82.9% were receiving 10 mg of Ramipril at 1 year, 74.8% at 2 years, 71.0% at 3 years, 62.8% at 4 years and 64.6% at last visit. Among those allocated to placebo, the proportion on open label ACE-I was 3.4%, 6.0%, 8.1%, 10.7% and 12.7% respectively. At the end of the study 1.6% of Ramipril patients and 1.9% of placebo patients were receiving an angiotensin-2 receptor antagonist. The most common reasons for discontinuing blinded medication are outlined in Table 2. More patients in the Ramipril group stopped medications for cough (7.2% v 1.7%) or hypertension (1.8% v 1.4%). By contrast, more placebo patients stopped blinded medication for uncontrolled hypertension (0.3% v 0.6%) or for a clinical event (1.9% v 2.4%). The proportions of patients receiving non-study ACE-I for heart failure was 3.3% in the active group and 4.5% in the placebo group, for proteinuria was 1.4% v 1.6%, and for control of hypertension 4.4% v 6.2%. The use of open label A-2 receptor antagonists in both groups was low (1.6% v 1.9%) but the reasons reflect a pattern similar to the use of ACE-inhibitors (heart failure 0.6% v 0.8%, hypertension 1.1% v 1.3%).

TABLE 2

Reasons for discontinuing blinded medication

| | Ramipril | Placebo |
|---|---|---|
| No. Randomized | 4645 | 4652 |
| No. Stopping at any time* | 1370 (33.0) | 1247 (30.7) |
| No. Permanently discontinuing* | 1207 (29.1) | 1087 (26.7) |
| Reasons for stopping | | |
| Cough | 335 (7.2%) | 81 (1.7%) |
| Hypotension/dizziness | 82 (1.8%) | 65 (1.4%) |
| Angioedema | 16 (0.3%) | 12 (0.3%) |
| Uncontrolled Hypertension | 16 (0.3%) | 30 (0.6%) |
| Clinical Events | 90 (1.9%) | 113 (2.4%) |
| Non-study ACE-I | 124 (2.7%) | 187 (4.0%) |
| Reasons for using open label ACE-I: | | |
| Heart Failure | 231 (5.0%) | 320 (6.9%) |
| Proteinuria | 63 (1.4) | 73 (1.6%) |
| Hypertension | 205 (4.4%) | 289 (6.2%) |

*% of alive

Example 4

Blood Pressure

The BP at entry was 139/79 in both groups. This decreased to 133/76 in the active group and 137/78 in the control group at 1 month, 135/76 and 138/78 at 2 years and 136/76 and 139/77 at the end of the study.

Example 5

Primary Outcomes and Total Mortality (Table 3)

There were 646 patients in the Ramipril group (13.9%) who suffered CV death, MI or stroke compared to 816 (17.5%) in the placebo group (RR of 0.78, 95% Cl of 0.70-0.86; p=0.000002). In addition there were highly significant reductions separately in CV mortality (278 v 371, RR of 0.75, 95% Cl of 0.64-0.87; p=0.0002), MI (453 v 559, RR of 0.80, 95% Cl of 0.71-0.91; p=0.0005) and stroke (155 v 225, RR of 0.68, 95% CL of 0.56-0.84; p=0.0001). All cause mortality was also significantly reduced (476 v 567, RR of 0.83, 95% Cl of 0.74-0.94; p=0.0035).

TABLE 3

Primary Outcome and its Components in the HOPE Study

|  | Ramipril | Placebo | RRR (95% CI) | Z | Log rank p |
|---|---|---|---|---|---|
| No. Randomized | 4645 | 4652 | | | |
| CV death, MI, Stroke* | 646 (13.9%) | 816 (17.5%) | 0.78 (0.70-0.86) | −4.75 | 0.000002 |
| CV death | 278 (6.0%) | 371 (8.0%) | 0.75 (0.64-0.87) | −3.72 | 0.0002 |
| MI | 453 (9.8%) | 559 (12.0%) | 0.80 (0.71-0.91) | −3.49 | 0.0005 |
| Strokes | 155 (3.3%) | 225 (4.8%) | 0.68 (0.56-0.84) | −3.70 | 0.0002 |
| Total mortality | 476 (10.3%) | 567 (12.2%) | 0.83 (0.74-0.94) | −2.92 | 0.0035 |

*There were an additional 34/244 events with low dose Ramipril. Inclusion of these events leads to 13.9% primary events with Ramipril v 17.5% with placebo (RRR of 0.78, 95% CI of 0.70-0.86). Note that patients could have experienced more than one event.

Example 6

Secondary and Other Outcomes (Table 4)

There was a significant reduction in the number of patients undergoing revascularization procedures (742 v 854, RR of 0.85, 95% Cl of 0.77-0.94; p=0.0013), and a trend to fewer HF hospitalizations (150 v 176; RR of 0.84, 95% Cl of 0.68 to 1.05; p=0.13). However, there was no impact on hospitalizations for unstable angina. There were also significant reductions in the number of patients with cardiac arrests (37 v 58, RR=0.63, p.0.03) worsening angina (1104 v 1220, RR=0.88, p=0.003), new heart failure (343 v 435, RR=0.78, p=0.0005), new diagnosis of diabetes (108 v 157, RR=0.69, p=0.003), or those experiencing diabetic complications (319 v 378, RR=0.85, p=0.018).

Example 7

Subgroup Analysis (Table 5)

The beneficial impact on the primary outcome was consistently observed among diabetic and nondiabetic patients; females and males, those with and without evidence of vascular disease, those under and over 65 years, those with and without hypertension at baseline and those with and without microalbuminuria at baseline. In addition, there was a clear benefit among both groups of patients entering the study with or without evidence of coronary artery disease, with and without an MI and among those (n=4676) with a documented EF≧0.40 (317/2339 v 427/2337, RR of 0.73, 95% Cl of 0.63-0.84, p=0.00002).

TABLE 4

Secondary and other Outcomes in the HOPE Study

|  | Ramipril | Placebo | RRR (95% CI) | Z | Log rank p |
|---|---|---|---|---|---|
| No. Randomized | 4645 | 4652 | | | |
| | | Secondary Outcomes | | | |
| Revascularization* | 742 (16.0%) | 854 (18.4%) | 0.85 (0.77-0.94) | −3.22 | 0.0013 |
| Unstable angina hospitalization* | 564 (12.1%) | 573 (12.3%) | 0.98 (0.87-1.10) | — | n.s. |
| Diabetic Complications+* | 298 (6.4%) | 357 (7.7%) | 0.83 (0.71-0.97) | −2.39 | 0.017 |
| Heart Failure Hospitalizations* | 150 (3.2%) | 176 (3.8%) | 0.84 (0.68-1.05) | −1.53 | 0.13 |
| | | Other Outcomes | | | |
| All Heart Failure** | 343 (7.4%) | 435 (9.4%) | 0.78 (0.67-0.90) | −3.51 | 0.0005 |
| Cardiac Arrests | 37 (0.8%) | 58 (1.2%) | 0.63 (0.42-0.96) | −2.19 | 0.03 |
| Worsening angina** | 1104 (23.8%) | 1220 (26.2%) | 0.88 (0.81-0.96) | −2.98 | 0.0029 |
| New diagnosis of diabetes | 108 (3.8%) | 157 (5.5%) | 0.69 (0.54-0.88) | −3.01 | 0.0026 |
| UA with ECG changes | 179 (3.4%) | 185 (4.0%) | 0.96 (0.78-1.18) | — | n.s. |

Centrally adjudicated events,
**Includes cases irrespective of hospitalization.
+Diabetic complications include diabetic nephropathy, renal dialysis and laser therapy for diabetic retinopathy.

TABLE 5

Impact of Ramipril compared to Placebo in Various Subgroups: Note the consistency of results and that the upper 95% CI is less than 1 in most instances.

| | No. of Patients | Placebo Rate | Primary Composite Outcome RRR (95% CI) |
|---|---|---|---|
| A) Prespecified Subgroups | | | |
| CVD+ | 8160 | 18.5 | 078 (0.71-0.87) |
| CVD− | 1137 | 10.1 | 0.81 (0.56-1.20) |
| Diabetes+ | 3578 | 19.6 | 0.76 (0.65-0.89) |
| Diabetes− | 5719 | 16.3 | 0.79 (0.69-0.91) |
| B) Other Subgroups | | | |
| Age <65 | 4169 | 14.0 | 0.82 (0.70-0.98) |
| Age 65+ | 5128 | 20.5 | 0.75 (0.66-0.85) |
| Male | 6817 | 18.5 | 0.79 (0.70-0.89) |
| Female | 2480 | 14.7 | 0.76 (0.61-0.95) |
| Hypertension+ | 4355 | 19.0 | 0.75 (0.65-0.87) |
| Hypertension− | 4942 | 16.3 | 0.81 (0.70-0.93) |
| CAD+ | 7475 | 18.4 | 0.80 (0.71-0.89) |
| CAD− | 1822 | 13.9 | 0.71 (0.54-0.93) |
| Prior MI+ | 4892 | 20.7 | 0.79 (0.69-0.90) |
| Prio MI− | 4405 | 14.0 | 0.77 (0.65-0.91) |
| Cerebro VD+ | 1013 | 25.5 | 0.73 (0.56-0.95) |
| Cerebro VD− | 8284 | 16.6 | 0.79 (0.71-0.88) |
| PVD+ | 4046 | 21.8 | 0.74 (0.64-0.86) |
| PVD− | 5251 | 14.1 | 0.84 (0.72-0.98) |
| MA+ | 1963 | 26.1 | 0.71 (0.59-0.86) |
| MA− | 7334 | 15.2 | 0.82 (0.72-0.92) |

CVD = Cardiovascular disease,
CAD = Coronary artery disease,
MA = Microalbuminuria,
PVD = Peripheral vascular disease Example 8

Time Course of Benefit

The reduction in the primary outcome was evident within 1 year after randomization (167 v 197, RR of 0.85; 95% Cl of 0.69 to 1.04), and became statistically significant at 2 years (323 v 396; RR of 0.81; 95% Cl of 0.70 to 0.94. Conditioned on survival up to the prior year, the relative risk in the second year was 0.78, in the third 0.74, and 0.73 in the fourth year.

Discussion

The HOPE trial conclusively proves that Ramipril, an ACE-I, is beneficial in a broad range of patients without evidence of LV systolic dysfunction or HF who are at high risk of future cardiovascular events. There are clear reductions in each of mortality, MI and strokes. Coronary revascularizations, cardiac arrests and development of heart failure are also clearly reduced. Ramipril also reduces the risk of diabetic complications; and the development of diabetes among non-diabetics.

Benefits of ACE-I Now Extend More Widely

These data substantially expand the population who would benefit from ACE-I and are complementary to previous studies in patients with low EF or HF and acute MI. The underlying rationale for the HOPE study was that ACE inhibition would prevent the events that related to ischemia and atherosclerosis, in addition to the heart failure and left ventricular dysfunction. To avoid potential confusion in the interpretation of the results of this study, we deliberately confined our trial to those without HF and excluded those with a known low EF. The study did include, however, the large number of individuals at risk of outcomes related to the progression of atherosclerosis and thrombotic vascular occlusion. Thus a broad range of patients with any manifestation of coronary artery disease (eg unstable angina, stable angina or previous revascularization), previous history of cerebrovascular disease or peripheral arterial disease were included. As a result, we have been able to demonstrate the value of ACE-I in a broad spectrum of patients with a range of clinical manifestations of atherosclerosis that increased the risk of CV death, MI or stroke. This approach is neither primary or secondary prevention, but is rather a high risk prevention strategy, which includes individuals with a high likelihood of a future event, rather than including patients solely by the presence of a specific risk factor or occurrence of a specific cardiovascular event. The present results attest to the success of this approach in identifying a high-risk population with a significant rate of CV endpoints who are likely to benefit from a therapy which prevents the progression of atherosclerosis or its complications. These findings along with those from previous trials are of major clinical importance and indicate that documentation of low EF on HF should not be a criterion to using ACE-I long term in patients who are at high risk of CV events, due to other clinical criteria.

There were 3578 diabetic patients entering our study, of whom 1100 had no clinical manifestations of CVD, and their risk of CV outcomes was lower by about half. Despite this, the RRR we observed was consistent with the overall benefit in the trial and among such diabetics the composite outcome of CV death, MI, stroke, heart failure, revascularization and diabetic complications was significantly reduced.

Benefits of ACE-I Similar to Other Preventive Strategies

The magnitude of benefit of ACE-I is at least as large as that observed with other proven secondary prevention measures such as betablockers (Yusuf S et al., Prog Cardiovasc Dis 1985; 27(5): 335-371), aspirin (BMJ 1994; 308(6921): 81-106) and lipid lowering (Law M. Lipids and cardiovascular disease. Chpt 13 In: Yusuf S, Cairns J A, Camm A J, Fallen E L, Gersh B J. (Eds), Evidence Based Cardiology. London: BMJ Books, 1998. Pg. 191-205) over a 4 year treatment period. Given the broad population in HOPE and previous trials of ACE-I, the very clear evidence of benefit in addition to other effective therapies and high tolerance, ACE-I have a major role in CV prevention and treatment. The relative risk reduction in the first year of the trial was about 11%, increasing to 22% (conditional RRR) in the $2^{nd}$ year, 26% in the $3^{rd}$ year and 27% in the $4^{th}$ year. These data indicate a very rapid emergence of benefit with increasing divergence in the second year which is at least maintained and perhaps increased in future years. This suggests that the benefits of ACE-I are likely to be sustained and perhaps enhanced on longer term treatment.

Benefits are Additional to Concomitant Proven Medications

The benefits of Ramipril were observed among patients receiving a number of effective treatments such as aspirin, betablockers and lipid lowering agents indicating that ACE inhibition offers an additional approach to prevent atherothrombotic complications. Only a small part of the reductions in CV mortality, MI and strokes could be attributed to BP reduction as the majority of patients entering the study were not hypertensive (by conventional definitions) and the difference in BP reduction was extremely modest (−3 systolic/−2 mmHg diastolic). A 2 mm reduction in diastolic BP reduction might at best explain about half in the reduction in stroke and about one-quarter of the reduction in myocardial infarction (Collins R. et al., Lancet 1990; 335(8693): 827-838). However, recent trials such as the Hypertension Optimum Treatment (Hansson L. et al., Lancet 1998; 351(9118):

1755-1762) have suggested that for high risk patients, eg diabetics, it may be beneficial to lower BP even within the "normal" range. Moreover, a recent reanalysis of the Framingham Heart Study based on 20 year BP data (Clarke R. et al., Am J Epidemiology 1999; 150(4): (In press) suggests that the degree of benefit expected from a lower BP may have been underestimated. Despite these considerations, it is possible that additional direct mechanisms of ACE-I on the heart or the vasculaturs is of importance. This includes antagonizing the direct effects of angiotensin-II on vasoconstriction, vascular smooth muscle proliferation (Lonn E M et al. Circulation 1994; 90(4): 2056-2069) and plaque rupture (Schieffer B. et al., Circulation (in press)); improvement in vascular endothelial function, reduction of LV hypertrophy and enhanced fibrinolysis (Lonn E M et al. Circulation 1994; 90(4): 2056-2069).

Also a reduction in the number of patients developing or being hospitalized for heart failure was observed in patients with no evidence of impairment of LV systolic function. These data complement the SOLVD Prevention Trial in patients with low EF, and the SAVE trials (low EF early post-MI) which demonstrated that ACE-I prevent the development of heart failure; and the trials in patients with documented low EF and HF which indicated a reduction in hospitalization for heart failure. HOPE and these studies indicate that ACE-I are likely to be of value among patients who are at high risk of developing heart failure irrespective of the degree of left ventricular systolic dysfunction. One issue that should be considered is the extent to which the results may have been affected by inclusion of individuals with undiagnosed low EF. This is likely to be very low because a) a large substudy in 3 centres involving 468 consecutive patients indicated that only 2.6% had an EF below 0.40, b) an extensive chart audit identified only <5% of patients with a low EF prior to randomization; and c) clear benefit (RR of 0.73, 95% Cl of 0.63 to 0.84; p=0.00002) was seen in the subgroup of patients (n=4676) with documented preserved ventricular function and also in those without previous MI. (RR of 0.79, 95% Cl of 0.69 to 0.90; p=0.0004)

Possible Mechanisms of Benefit in Diabetes

A marked reduction in the number of patients developing diabetic complications and the number being newly diagnosed as having diabetes was observed. These effects may be mediated through improved insulin sensitivity or a decrease in hepatic clearance of insulin. The results are also consistent with the results of the recent Captopril Prevention Project trial (Hansson L. et al., Lancet 1999; 353(9153): 611-616), which indicated a reduction in newly diagnosed diabetes in patients randomized to captopril compared to a diuretic or beta blocker, and other trials indicating that the progression of diabetic nephropathy among type II diabetics treated with an ACE-inhibitor is reduced (Ruggenenti P. et al. Lancet 1999; 354 (9176): 359-364).

Safety and Tolerability

The ACE-inhibitor Ramipril, was generally well tolerated in the trial. Apart from an increase in the number of patients stopping Ramipril for cough (excess of 5%), no other side effect was significantly more frequent. There was a small nonsignificant increase in the number of patients stopping medication for dizziness/hypotension (0.3%). The majority of patients (approximately 80%) remained on an ACE-I over the 4.2 year duration of the trial.

Conclusion

The HOPE study clearly demonstrates that Ramipril, a long acting ACE-inhibitor, reduces mortality, MI, strokes, revascularization rates, cardiac arrests, new heart failure and diabetic complications in a broad spectrum of high risk patients. Treating 1000 patients with ACE-inhibitors for 4 years prevents 160 patients from experiencing any one of the above events.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims, be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

We claim:

1. A method for reducing the risk of a cardiovascular event in a patient with an increased cardiovascular risk and no evidence of left ventricular dysfunction, which comprises administering to the patient an effective amount of at least one ACE inhibitor chosen from ramipril, ramiprilat, pharmaceutically acceptable salts of ramipril, and pharmaceutically acceptable salts of ramiprilat, wherein the cardiovascular event is stroke, cardiovascular death or myocardial infarction.

2. A method according to claim 1, where the patient has an increased cardiovascular risk due to a manifest coronary heart disease, a history of transient ischaemic attacks or stroke or a history of peripheral vascular disease.

3. A method according to claim 1, where the patient is diabetic.

4. A method according to claim 3, where the patient has at least one other risk factor.

5. A method according to claim 4, where the other risk factor is chosen from current or previous hypertension, elevated total cholesterol, low HDL cholesterol, current cigarette smoking, known microalbuminuria and previous vascular disease.

6. A method according to claim 1, where the patient is non-hypertensive.

7. A method according to claim 1, where the patient is older than 55 years.

8. A method according to claim 1, which further comprises administering a cholesterol lowering agent to the patient.

9. A method according to claim 8, where the cholesterol lowering agent is a statin.

10. A method according to claim 9, where the statin is lovastatin, pravastatin, simvastatin, fluvastatin or mixtures thereof.

11. A method according to claim 10, where the statin is pravastatin.

12. A method according to claim 10, where the statin is simvastatin.

13. A method according to claim 1, which further comprises administering a calcium channel blocker or a beta blocker to the patient.

14. A method according to claim 1, which further comprises administering, an antihypertensive, a diuretic or aspirin to the patient.

15. A method according to claim 1, wherein the ACE inhibitor is ramipril.

16. A method according to claim 1, wherein the ACE inhibitor is ramiprilat.

17. A method according to claim 1, wherein the cardiovascular event is stroke.

18. A method according to claim 1, wherein the cardiovascular event is cardiovascular death.

19. A method according to claim 1, wherein the cardiovascular event is myocardial infarction.

20. A method for reducing the risk of a cardiovascular event in a patient with an increased cardiovascular risk and no evidence of left ventricular dysfunction, which comprises administering to the patient an effective amount of at least one ACE inhibitor chosen from ramipril, ramiprilat, pharmaceutically acceptable salts of ramipril, and pharmaceutically acceptable salts of ramiprilat, wherein the cardiovascular event is congestive heart failure, worsening of angina, cardiac arrest or a revascularization procedure.

21. A method according to claim 20, where the revascularization procedure is coronary artery bypass graft surgery, percutaneous transluminal coronary angioplasty, peripheral angioplasty surgery, amputation or carotid endarterectomy.

22. A method according to claim 20, where the patient has an increased cardiovascular risk due to a manifest coronary heart disease, a history of transient ischaemic attacks or stroke or a history of peripheral vascular disease.

23. A method according to claim 20, where the patient is diabetic.

24. A method according to claim 23, where the patient has at least one other risk factor.

25. A method according to claim 24, where the other risk factor is chosen from current or previous hypertension, elevated total cholesterol, low HDL cholesterol, current cigarette smoking, known microalbuminuria and previous vascular disease.

26. A method according to claim 20, where the patient is non-hypertensive.

27. A method according to claim 20, where the patient is older than 55 years.

28. A method according to claim 20, which further comprises administering a cholesterol lowering agent to the patient.

29. A method according to claim 28, where the cholesterol lowering agent is a statin.

30. A method according to claim 29, where the statin is lovastatin, pravastatin, simvastatin, fluvastatin or mixtures thereof.

31. A method according to claim 30, where the statin is pravastatin.

32. A method according to claim 30, where the statin is simvastatin.

33. A method according to claim 20, which further comprises administering a calcium channel blocker or a beta blocker to the patient.

34. A method according to claim 20, which further comprises administering an antihypertensive, a diuretic or aspirin to the patient.

35. A method according to claim 20, wherein the ACE inhibitor is ramipril.

36. A method according to claim 20, wherein the ACE inhibitor is ramiprilat.

37. A method according to claim 1, wherein the ACE inhibitor is administered in an amount from about 0.01 mg/kg/day to about 1 mg/kg/day.

38. A method according to claim 15, wherein the ramipril is administered in an amount of 2.5 mg/day.

39. A method according to claim 15, wherein the ramipril is administered in an amount of 5 mg/day.

40. A method according to claim 15, wherein the ramipril is administered in an amount of 10 mg/day.

41. A method according to claim 1, wherein the ACE inhibitor is administered in a tablet.

42. A method according to claim 1, wherein the ACE inhibitor is administered in a capsule.

43. A method according to claim 20, wherein the ACE inhibitor is administered in an amount from about 0.01 mg/kg/day to about 1 mg/kg/day.

44. A method according to claim 35, wherein the ramipril is administered in an amount of 2.5 mg/day.

45. A method according to claim 35, wherein the ramipril is administered in an amount of 5 mg/day.

46. A method according to claim 35, wherein the ramipril is administered in an amount of 10 mg/day.

47. A method according to claim 20, wherein the ACE inhibitor is administered in a tablet.

48. A method according to claim 20, wherein the ACE inhibitor is administered in a capsule.

49. A method for reducing the risk of a cardiovascular event in a patient who exhibits no left ventricular dysfunction, which comprises administering to the patient an effective amount of at least one ACE inhibitor chosen from ramipril, ramiprilat, pharmaceutically acceptable salts of ramipril, and pharmaceutically acceptable salts of ramiprilat,
  wherein the patient has an increased cardiovascular risk due to at least two risk factors chosen from a history of coronary heart disease, a history of transient ischaemic attacks, a history of stroke, and a history of peripheral vascular disease; and
  wherein the cardiovascular event is stroke, cardiovascular death or myocardial infarction.

50. A method according to claim 49, where the patient is diabetic.

51. A method according to claim 50, where the patient has at least one other risk factor.

52. A method according to claim 51, where the other risk factor is chosen from current or previous hypertension, elevated total cholesterol, low HDL cholesterol, current cigarette smoking, known microalbuminuria and previous vascular disease.

53. A method according to claim 49, where the patient is non-hypertensive.

54. A method according to claim 49, where the patient is older than 55 years.

55. A method according to claim 49, which further comprises administering a cholesterol lowering agent to the patient.

56. A method according to claim 55, where the cholesterol lowering agent is a statin.

57. A method according to claim 56, where the statin is lovastatin, pravastatin, simvastatin, fluvastatin or mixtures thereof.

58. A method according to claim 57, where the statin is pravastatin.

59. A method according to claim 57, where the statin is simvastatin.

60. A method according to claim 49, which further comprises administering a calcium channel blocker or a beta blocker to the patient.

61. A method according to claim 49, which further comprises administering an antihypertensive, a diuretic or aspirin to the patient.

62. A method according to claim 49, wherein the ACE inhibitor is ramipril.

63. A method according to claim 62, wherein the ramipril is administered in an amount of 2.5 mg/day.

64. A method according to claim 62, wherein the ramipril is administered in an amount of 5 mg/day.

65. A method according to claim 62, wherein the ramipril is administered in an amount of 10 mg/day.

66. A method according to claim 49, wherein the ACE inhibitor is ramiprilat.

67. A method according to claim 49, wherein the cardiovascular event is stroke.

68. A method according to claim 49, wherein the cardiovascular event is cardiovascular death.

69. A method according to claim 49, wherein the cardiovascular event is myocardial infarction.

70. A method according to claim 49, wherein the ACE inhibitor is administered in an amount from about 0.01 mg/kg/day to about 1 mg/kg/day.

71. A method according to claim 49, wherein the ACE inhibitor is administered in a tablet.

72. A method according to claim 49, wherein the ACE inhibitor is administered in a capsule.

73. A method for reducing the risk of a cardiovascular event in a patient who exhibits no left ventricular dysfunction, which comprises administering to the patient an effective amount of at least one ACE inhibitor chosen from ramipril, ramiprilat, pharmaceutically acceptable salts of ramipril, and pharmaceutically acceptable salts of ramiprilat,
   wherein the patient has an increased cardiovascular risk due to at least two risk factors chosen from a history of coronary disease, a history of transient ischaemic attacks, a history of stroke, and a history of peripheral vascular disease; and
   wherein the cardiovascular event is congestive heart failure, worsening of angina, cardiac arrest or a revascularization procedure.

74. A method according to claim 73, where the revascularization procedure is coronary artery bypass graft surgery, percutaneous transluminal coronary angioplasty, peripheral angioplasty surgery, amputation or carotid endarterectomy.

75. A method according to claim 74, where the patient is diabetic.

76. A method according to claim 75, where the patient has at least one other risk factor.

77. A method according to claim 76, where the other risk factor is chosen from current or previous hypertension, elevated total cholesterol, low HDL cholesterol, current cigarette smoking, known microalbuminuria and previous vascular disease.

78. A method according to claim 73, where the patient is non-hypertensive.

79. A method according to claim 73, where the patient is older than 55 years.

80. A method according to claim 73, which further comprises administering a cholesterol lowering agent to the patient.

81. A method according to claim 80, where the cholesterol lowering agent is a statin.

82. A method according to claim 81, where the statin is lovastatin, pravastatin, simvastatin, fluvastatin or mixtures thereof.

83. A method according to claim 82, where the statin is pravastatin.

84. A method according to claim 82, where the statin is simvastatin.

85. A method according to claim 73, which further comprises administering a calcium channel blocker or a beta blocker to the patient.

86. A method according to claim 73, which further comprises administering an antihypertensive, a diuretic or aspirin to the patient.

87. A method according to claim 73, wherein the ACE inhibitor is ramipril.

88. A method according to claim 87, wherein the ramipril is administered in an amount of 2.5 mg/day.

89. A method according to claim 87, wherein the ramipril is administered in an amount of 5 mg/day.

90. A method according to claim 87, wherein the ramipril is administered in an amount of 10 mg/day.

91. A method according to claim 73, wherein the ACE inhibitor is ramiprilat.

92. A method according to claim 73, wherein the ACE inhibitor is administered in an amount from about 0.01 mg/kg/day to about 1 mg/kg/day.

93. A method according to claim 73, wherein the ACE inhibitor is administered in a tablet.

94. A method according to claim 73, wherein the ACE inhibitor is administered in a capsule.

* * * * *

UNITED STATES PATENT AND TRADEMARK OFFICE
CERTIFICATE OF CORRECTION

PATENT NO. : 7,368,469 B2 Page 1 of 1
APPLICATION NO. : 11/490061
DATED : May 6, 2008
INVENTOR(S) : Schölkens et al.

It is certified that error appears in the above-identified patent and that said Letters Patent is hereby corrected as shown below:

On the title page, item (57), line 8, "renin angiotensin" should read --renin-angiotensin--.

On the title page, item (57), line 12, "containing an an inhibitor" should read --containing an inhibitor--.

In claim 14, column 18, line 64, "administering, an" should read --administering an--.

Signed and Sealed this

Fifteenth Day of July, 2008

JON W. DUDAS
*Director of the United States Patent and Trademark Office*